United States Patent
Ohishi et al.

(10) Patent No.: US 10,022,096 B2
(45) Date of Patent: Jul. 17, 2018

(54) MEDICAL IMAGE PROCESSING APPARATUS, X-RAY DIAGNOSTIC APPARATUS, MEDICAL IMAGE PROCESSING METHOD, AND X-RAY DIAGNOSTIC METHOD

(71) Applicant: Toshiba Medical Systems Corporation, Otawara-shi (JP)

(72) Inventors: Satoru Ohishi, Otawara (JP); Ryoichi Nagae, Nasushiobara (JP); Yuichiro Watanabe, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 122 days.

(21) Appl. No.: 14/865,759

(22) Filed: Sep. 25, 2015

(65) Prior Publication Data
US 2016/0089097 A1    Mar. 31, 2016

(30) Foreign Application Priority Data
Sep. 29, 2014    (JP) .................................. 2014-199488

(51) Int. Cl.
*A61B 6/00*    (2006.01)
*G06T 11/00*    (2006.01)
(Continued)

(52) U.S. Cl.
CPC ............ *A61B 6/504* (2013.01); *A61B 6/4435* (2013.01); *A61B 6/4441* (2013.01);
(Continued)

(58) Field of Classification Search
CPC ... A61B 6/4435; A61B 6/4441; A61B 6/4447; A61B 6/461; A61B 6/481; A61B 6/504;
(Continued)

(56) References Cited

U.S. PATENT DOCUMENTS 4,633,307 A * 12/1986 Honda ................... A61B 6/504
378/98.12
5,377,681 A * 1/1995 Drane ................... G01T 1/1642
600/419

(Continued)

FOREIGN PATENT DOCUMENTS

WO    WO 2014/168148 A1    10/2014

OTHER PUBLICATIONS

U.S. Appl. No. 14/878,662, filed Oct. 8, 2015, Ohishi.

*Primary Examiner* — Allen C. Ho
(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry obtains time changes in intensity of image signals corresponding to a contrast agent or a blood flow based on at least one of time series contrast image data, time series non-contrast image data, and time series subtraction image data between the contrast image data and the non-contrast image data, generate color image data, having color pixel values based on the time changes in the image signals, according to a color scale, and display frames of the color image data sequentially on a display. The processing circuitry performs a loop playing of the frames of the color image data by sequentially shifting the color scale in a direction of a color phase change, at pixels of the color image data, until an instruction for stopping the loop playing is input from an input circuit.

21 Claims, 13 Drawing Sheets

(51) Int. Cl.
*G09G 5/02* (2006.01)
*G09G 5/14* (2006.01)

(52) U.S. Cl.
CPC ............ *A61B 6/4447* (2013.01); *A61B 6/461* (2013.01); *A61B 6/481* (2013.01); *A61B 6/486* (2013.01); *A61B 6/487* (2013.01); *A61B 6/52* (2013.01); *A61B 6/5205* (2013.01); *A61B 6/5211* (2013.01); *A61B 6/5235* (2013.01); *G06T 11/001* (2013.01); *G06T 11/008* (2013.01); *G09G 5/02* (2013.01); *G09G 5/026* (2013.01); *G09G 5/14* (2013.01); *G06T 2211/404* (2013.01); *G09G 2340/06* (2013.01); *G09G 2340/08* (2013.01); *G09G 2340/125* (2013.01); *G09G 2340/14* (2013.01); *G09G 2380/08* (2013.01)

(58) Field of Classification Search
CPC ....... A61B 6/52; A61B 6/5205; A61B 6/5211; A61B 6/486; A61B 6/487; A61B 6/5235
USPC .......................................... 378/42, 62, 98.12
See application file for complete search history.

(56) References Cited

U.S. PATENT DOCUMENTS

| | | | | |
|---|---|---|---|---|
| 5,600,452 A * | 2/1997 | Simnon | ................. | A61B 6/481 348/E5.089 |
| 6,721,590 B2 * | 4/2004 | Ohishi | ................. | A61B 6/466 600/425 |
| 7,738,626 B2 * | 6/2010 | Weese | ................. | A61B 6/481 378/41 |
| 7,949,170 B2 * | 5/2011 | Goto | ................. | A61B 5/02007 382/131 |
| 8,050,474 B2 * | 11/2011 | Baumgart | ................. | G06T 5/50 382/130 |
| 8,073,224 B2 * | 12/2011 | Strobel | ................. | A61B 6/469 382/130 |
| 8,150,125 B2 * | 4/2012 | Baumgart | ................. | A61B 6/481 378/98.12 |
| 8,463,012 B2 * | 6/2013 | Rauch | ................. | G06T 7/38 378/4 |
| 8,509,384 B2 * | 8/2013 | Spahn | ................. | A61B 6/481 378/98.12 |
| 8,594,271 B2 * | 11/2013 | Sakaguchi | ................. | A61B 6/4441 378/4 |
| 8,731,262 B2 * | 5/2014 | Rauch | ................. | G06T 7/254 382/130 |
| 8,761,471 B2 * | 6/2014 | Ozawa | ................. | A61B 6/487 382/128 |
| 8,891,843 B2 * | 11/2014 | Ohishi | ................. | A61B 6/032 382/128 |
| 8,929,632 B2 | 1/2015 | Horz et al. | | |
| 8,948,475 B2 * | 2/2015 | Ostermeier | ................. | A61B 6/463 382/128 |
| 9,230,323 B2 * | 1/2016 | Kobayashi | ................. | A61B 6/481 |
| 9,433,392 B2 * | 9/2016 | Ohishi | ................. | A61B 6/463 |
| 9,433,393 B2 * | 9/2016 | Takemoto | ................. | A61B 6/481 |
| 9,443,330 B2 * | 9/2016 | Heigl | ................. | G06T 11/008 |
| 9,460,500 B2 * | 10/2016 | Ohishi | ................. | A61B 6/032 |
| 9,538,977 B2 * | 1/2017 | Sato | ................. | A61B 6/542 |
| 9,561,011 B2 * | 2/2017 | Arakita | ................. | A61B 6/504 |
| 9,576,350 B2 * | 2/2017 | Abe | ................. | A61B 6/481 |
| 9,734,578 B2 * | 8/2017 | Ohyu | ................. | G06T 7/0016 |
| 9,833,211 B2 * | 12/2017 | Nagae | ................. | A61B 6/507 |
| 9,833,212 B2 * | 12/2017 | Nagae | ................. | A61B 6/5211 |
| 9,907,525 B2 * | 3/2018 | Ohishi | ................. | A61B 6/504 |

* cited by examiner

MEDICAL IMAGE PROCESSING APPARATUS, X-RAY DIAGNOSTIC APPARATUS, MEDICAL IMAGE PROCESSING METHOD, AND X-RAY DIAGNOSTIC METHOD

CROSS REFERENCES TO RELATED APPLICATIONS

This application is based upon and claims the benefit of priority from Japanese Patent Application No. 2014-199488, filed on Sep. 29, 2014; the entire contents of which are incorporated herein by reference.

FIELD

Embodiments described herein relate generally to a medical image processing apparatus, an X-ray diagnostic apparatus, a medical image processing method, and an X-ray diagnostic method.

BACKGROUND

DSA (Digital Subtraction Angiography) is known as one of imaging methods for blood vessels in an X-ray diagnostic apparatus. DSA is the technology to acquire subtraction image data between frames of X-ray image data before and after injecting a contrast agent into an object, for diagnosis. That is, X-ray image data are acquired before injecting a contrast agent as mask image data for generating subtraction image data. After that, X-ray contrast image data are acquired continuously with injecting the contrast agent. Then, DSA image data, which are also called subtraction image data, are generated for diagnosis by subtraction processing between the X-ray contrast image data and the mask image data.

On the other hand, not only CTA (computed tomography angiography) in an X-ray CT (computed tomography) apparatus and contrast MRA (magnetic resonance angiography) in an MRI (magnetic resonance imaging) apparatus but also non-contrast MRA as though contrast imaging had been performed are also well known. The contrast image data assume to include the non-contrast MRA data from now on. In a case of contrast imaging, non-contrast image data are acquired before injecting a contrast agent. Then, a contrast agent is injected, and contrast image data are acquired continuously. Thus, subtraction image data are generated for diagnosis, by subtraction processing between contrast image data and non-contrast image data.

Such subtraction image data can be generated as image data in which unnecessary anatomical structures in observation of a blood vessel have been removed. That is, diagnostic image data in which blood vessels enhanced by a contrast agent have been depicted selectively can be obtained.

An object of the present invention is to display images which are more useful for diagnosis of a blood vessel, especially for perceiving a blood flow pattern.

DETAILED DESCRIPTION

Figure 1:
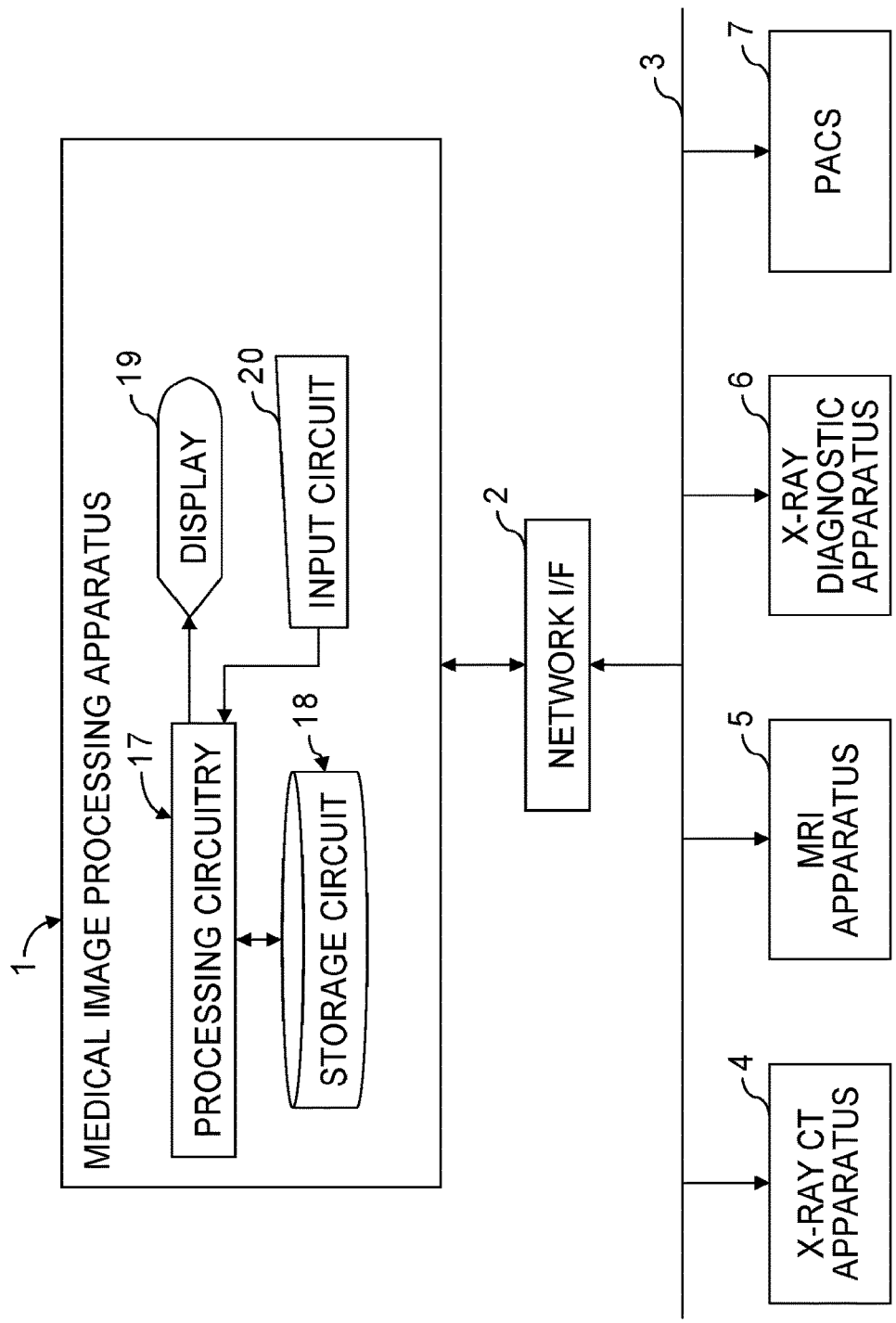
FIG. 1 is a configuration diagram of a medical image processing apparatus according to an embodiment of the present invention.

In general, according to one embodiment, a medical image processing apparatus includes processing circuitry. The processing circuitry is configured to obtain time changes in intensity of image signals corresponding to a contrast agent or a blood flow based on at least one of time series contrast image data of an object, time series non-contrast image data of the object, and time series subtraction image data of the object between the contrast image data and the non-contrast image data, generate color image data, having color pixel values based on the time changes in the image signals, according to a color scale, and display frames of the color image data sequentially on a display. The processing circuitry is configured to perform a loop playing of the frames of the color image data by sequentially shifting the color scale in a direction of a color phase change. The color scale is shifted gradually frame-by-frame, and pixels of the color image data are mapped to arbitrary colors according to the color scale. The loop playing is performed until an instruction for stopping the loop playing is input from an input circuit.

Further, according to one embodiment, an X-ray diagnostic apparatus includes an X-ray tube, an X-ray detector and processing circuitry. An imaging system consists of the X-ray tube and the X-ray detector acquires at least time series X-ray contrast image data of an object. The processing circuitry is configured to obtain time changes in concentration of a contrast agent based on the X-ray contrast image data or subtraction image data between the X-ray contrast image data and X-ray non-contrast image data; generate color image data, having color pixel values based on the time changes in the concentration of the contrast agent, according to a color scale; and display frames of the color image data sequentially on a display. The processing circuitry is configured to perform a loop playing of the frames of the color image data by sequentially shifting the color scale in a direction of a color phase change. The color scale is shifted gradually frame-by-frame, and pixels of the color image data are mapped to arbitrary colors according to the color scale. The loop playing is performed until an instruction for stopping the loop playing is input from an input circuit.

Further, according to one embodiment, a medical image processing method includes; obtaining time changes in intensity of image signals corresponding to a contrast agent or a blood flow based on at least one of time series contrast image data of an object, time series non-contrast image data of the object, and time series subtraction image data of the object between the contrast image data and the non-contrast image data; generating color image data, having color pixel values based on the time changes in the image signals, according to a color scale; and displaying frames of the color image data sequentially on a display. A loop playing of the frames of the color image data is performed by sequentially shifting the color scale in a direction of a color phase change. The color scale is shifted gradually frame-by-frame, and pixels of the color image data are mapped to arbitrary colors according to the color scale. The loop playing is performed until an instruction for stopping the loop playing is input from an input circuit.

Further, according to one embodiment, an X-ray diagnostic method includes: acquiring at least time series X-ray contrast image data of an object; obtaining time changes in concentration of a contrast agent based on the X-ray contrast image data or subtraction image data between the X-ray contrast image data and X-ray non-contrast image data; generating color image data, having color pixel values based on the time changes in the concentration of the contrast agent, according to a color scale; and displaying frames of the color image data sequentially on a display. A loop playing of the frames of the color image data is performed by sequentially shifting the color scale in a direction of a color phase change. The color scale is shifted gradually frame-by-frame, and pixels of the color image data are mapped to arbitrary colors according to the color scale. The loop playing is performed until an instruction for stopping the loop playing is input from an input circuit.

A medical image processing apparatus, an X-ray diagnostic apparatus, a medical image processing method, and an X-ray diagnostic method according to embodiments of the present invention will be described with reference to the accompanying drawings.

(Configuration and Function)

FIG. 1 is a configuration diagram of a medical image processing apparatus according to an embodiment of the present invention.

A medical image processing apparatus 1 is connected with a network 3 through a network I/F (interface) 2. Besides the medical image processing apparatus 1, medical equipments, such as image diagnostic apparatuses and a medical image server, are connected with the network 3. In the example shown in FIG. 1, an X-ray CT apparatus 4, an MRI apparatus 5 and an X-ray diagnostic apparatus 6 as image diagnostic apparatuses have been connected with the network 3. Furthermore, a PACS (picture archiving and communication system) 7 as a medical image server has been connected with the network 3.

Therefore, the medical image processing apparatus 1 can take desired medical image data, through the network 3, from a desired medical equipment connected with the network 3. The medical image processing apparatus 1 may also be built in an image diagnostic apparatus, such as the X-ray diagnostic apparatus 6, or a medical image server.

Figure 2:
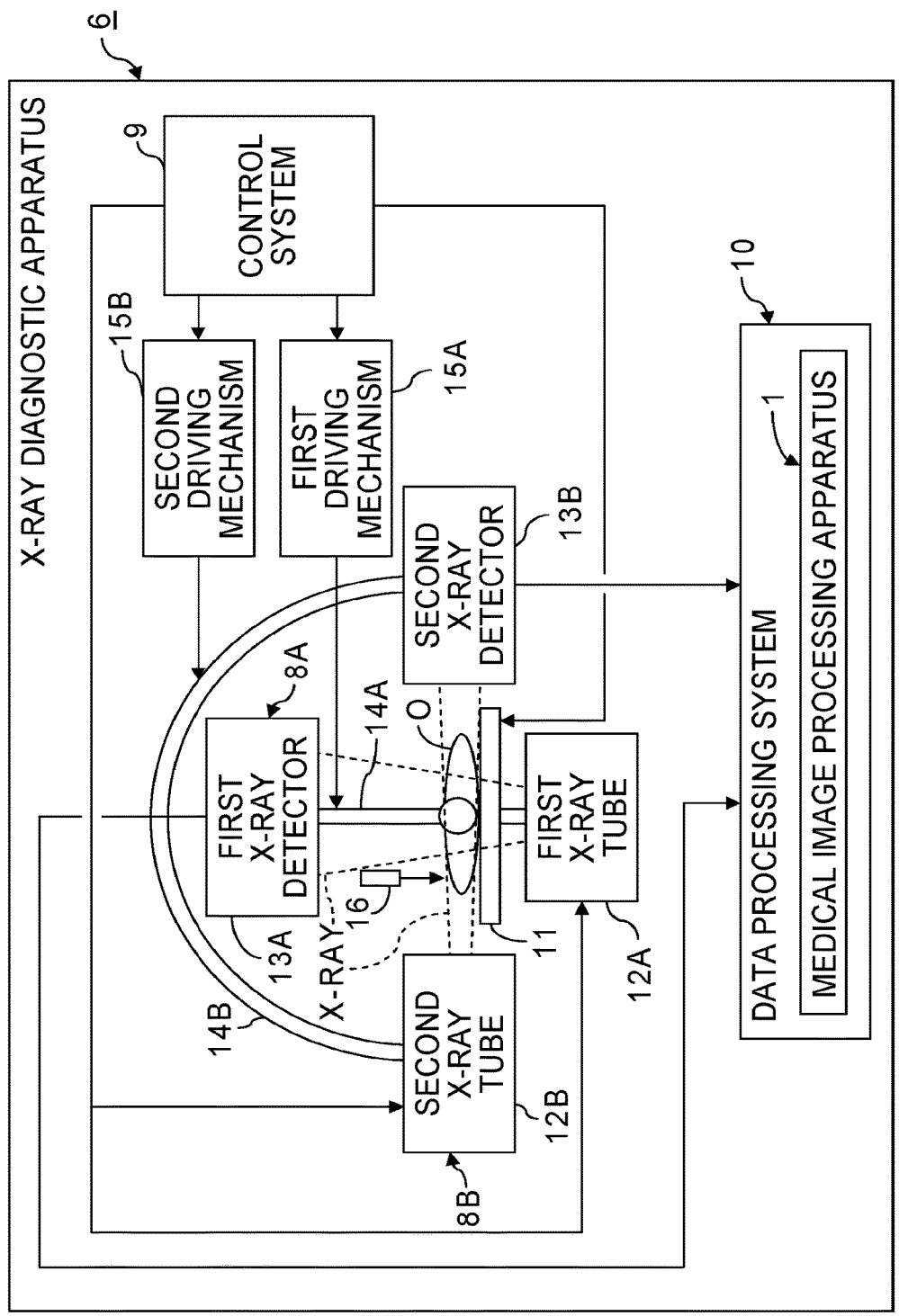
FIG. 2 shows an example of having the medical image processing apparatus shown in FIG. 1 built in the biplane type of X-ray diagnostic apparatus.

FIG. 2 shows an example of having the medical image processing apparatus 1 shown in FIG. 1 built in the biplane type of X-ray diagnostic apparatus 6.

The biplane type of X-ray diagnostic apparatus 6 includes two imaging systems 8A and 8B, a control system 9, a data processing system 10 and a bed 11. The first imaging system 8A is composed of the first X-ray tube 12A and the first X-ray detector 13A held by the first support mechanism 14A, such as a C-shaped arm. The first support mechanism 14A can be driven by the first driving mechanism 15A. Similarly, the second imaging system 8B is composed of the second X-ray tube 12B and the second X-ray detector 13B held by the second support mechanism 14B, such as a C-shaped arm. The second support mechanism 14B can be driven by the second driving mechanism 15B.

The control system 9 controls the two imaging systems 8A, 8B and the bed 11. For example, high voltages are applied to the first X-ray tube 12A and the second X-ray tube 12B from high voltage generators included in the control system 9 at predetermined timing according to imaging conditions of X-ray imaging. Furthermore, the first driving mechanism 15A and the second driving mechanism 15B are controlled by the control system 9 according to imaging conditions of X-ray imaging so that X-rays are exposed from predetermined positions and directions to imaging positions of an object O set on a top plate of the bed 11.

The data processing system 10 generates the first X-ray image data based on X-ray detection data detected by the first X-ray detector 13A and generates the second X-ray image data based on X-ray detection data detected by the second X-ray detector 13B.

The X-ray diagnostic apparatus 6 also includes a contrast agent injector 16. Therefore, X-ray contrast image data of the object O can be acquired by X-ray imaging with injecting a contrast agent into the object O.

In a typical biplane type of X-ray diagnostic apparatus 6, X-ray image data in the F (frontal) side of the object O can be acquired by the first imaging system 8A. Meanwhile, X-ray image data in the L (lateral) side of the object O can be acquired by the second imaging system 8B.

The medical image processing apparatus 1 can be built in the X-ray diagnostic apparatus 6 by installing a medical image processing program on a computer configuring the data processing system 10 of the X-ray diagnostic apparatus 6. As a matter of course, the medical image processing apparatus 1 may be built in not only the biplane type of X-ray diagnostic apparatus 6 but also a single plane type of X-ray diagnostic apparatus 6 having a single imaging system.

The independent medical image processing apparatus 1 as exemplified in FIG. 1 can also be configured by installing a medical image processing program on a computer, such as a workstation. The medical image processing program can also be recorded in an information recording medium to be distributed as a program product so that a general purpose computer can be used as the medical image processing apparatus 1.

As described above, circuitry, such as a computer, can be used for configuring the medical image processing apparatus 1 built in an image diagnostic apparatus or the like, or the independent medical image processing apparatus 1. When the medical image processing apparatus 1 is configured by circuitry, the medical image processing apparatus 1 includes processing circuitry 17, a storage circuit 18, a display 19 and an input circuit 20, as shown in FIG. 1.

The processing circuitry 17 consists of a circuit or a plurality of circuits. For example, the processing circuitry 17 can be configured by at least one CPU (central processing unit), at least one GPU (graphics processing unit), at least one ASIC (application specific integrated circuit), and/or at least one PLD (programmable logic device), such as an SPLD (simple PLD), a CPLD (complex PLD) and an FPGA (field programmable gate array).

Meanwhile, the input circuit 20 is a trackball, a switch button, a mouse, a keyboard, a touch panel, a touchpad or the like, for setting an ROI (region of interest) or the like. The input circuit 20 is coupled to the processing circuitry 17 so that the input circuit 20 can convert an input operation by an operator into an electric signal to output the electric signal to the processing circuitry 17.

Figure 3:
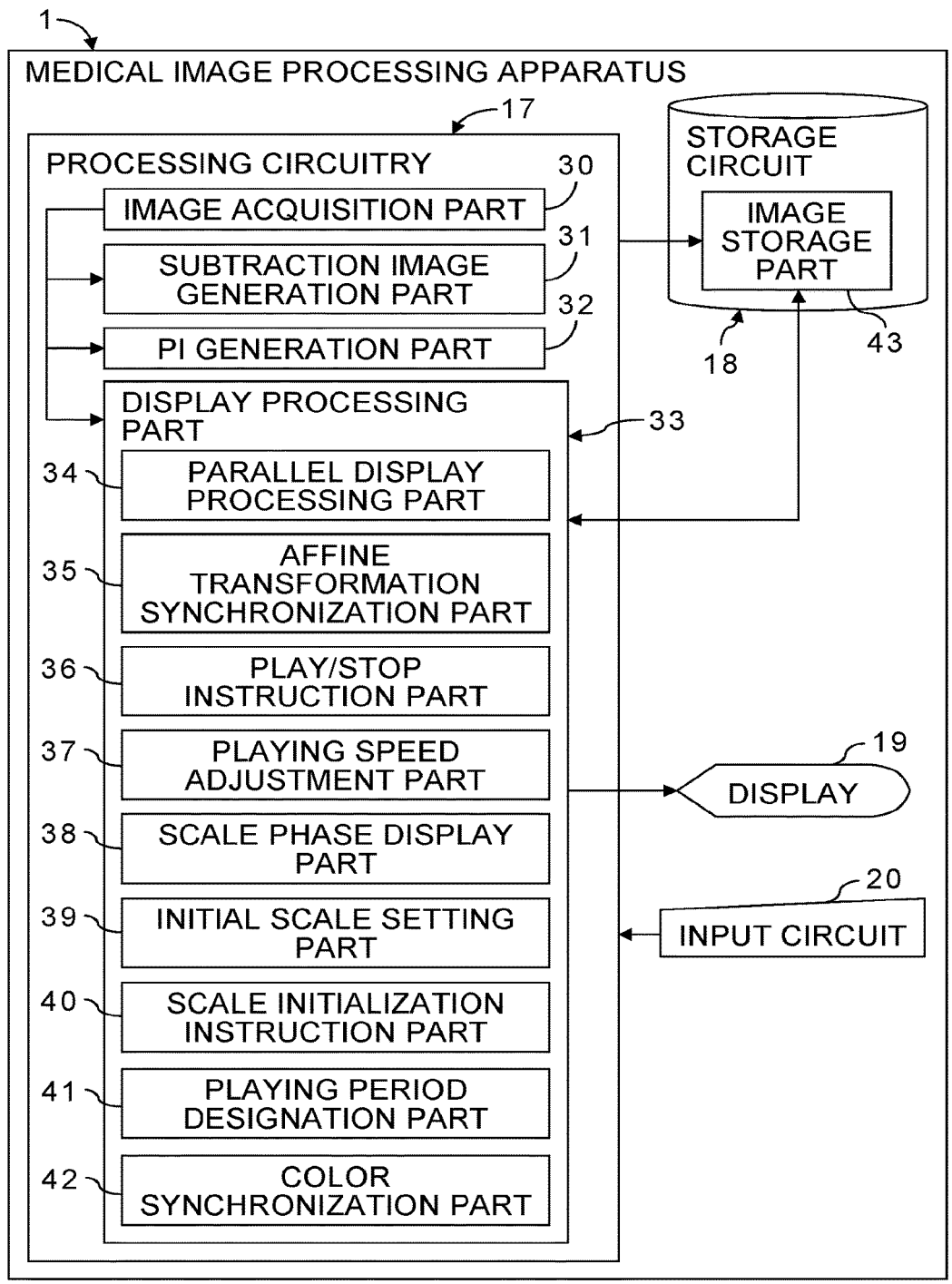
FIG. 3 is a detailed configuration diagram of the medical image processing apparatus shown in FIG. 1.

FIG. 3 is a detailed configuration diagram of the medical image processing apparatus 1 shown in FIG. 1.

The processing circuitry 17 executing a medical image processing program functions as an image acquisition part 30, a subtraction image generation part 31, a PI (parametric imaging) generation part 32 and a display processing part 33. The medical image processing program is stored in the storage circuit 18, such as a hard disk, included in the medical image processing apparatus 1. The display processing part 33 has a parallel display processing part 34, an affine transformation synchronization part 35, a play/stop instruction part 36, a playing speed adjustment part 37, a scale phase display part 38, an initial scale setting part 39, a scale initialization instruction part 40, a playing period designation part 41 and a color synchronization part 42. Meanwhile, the storage circuit 18 functions as an image storage part 43.

Note that, instead of storing programs in the storage circuit 18, the processing circuitry 17 may directly incorporate programs. In this case, the processing circuitry 17 achieves the functions by reading and executing the incorporated programs.

The image acquisition part 30 has a function to obtain desired medical image data from an image diagnostic apparatus, such as the X-ray diagnostic apparatus 6, or the PACS 7 through the network 3, and store the obtained medical image data in the image storage part 43. In particular, the image acquisition part 30 has a function to obtain medical moving image data, i.e., time series medical image data, showing a blood flow dynamic state of an object, acquired by contrast imaging or non-contrast imaging, from a desired medical equipment. The medical moving image data may be time series volume image data or time series 2D (two dimensional) image data.

For example, the image acquisition part 30 can obtain contrast image data, such as time series X-ray contrast CTA image data, time series contrast MRA image data or time series X-ray contrast image data, acquired by contrast imaging of an object using the X-ray CT apparatus 4, the MRI apparatus 5 or the X-ray diagnostic apparatus 6 respectively. Alternatively, the image acquisition part 30 can also obtain time series non-contrast MRA image data, acquired by non-contrast imaging of an object using the MRI apparatus 5, with applying TAG pulses as non-contrast image data which are similar to contrast image data.

Alternatively, at least time series contrast image data of an object may also be acquired previously by an imaging system coupled to the medical image processing apparatus 1, instead of obtaining contrast image data or subtraction image data in the image acquisition part 30. When an image diagnostic apparatus is the X-ray diagnostic apparatus 6, at least time series X-ray contrast image data of an object are acquired by an imaging system.

In a case of generating subtraction image data between contrast image data and non-contrast image data, the image acquisition part 30 obtains non-contrast image data and corresponding contrast image data separately, or non-contrast image data and corresponding contrast image data as a series of image data, from a corresponding medical equipment through the network 3.

Alternatively, the image acquisition part 30 may also obtain only contrast image data from a corresponding medical equipment through the network 3. In this case, image data, which have been relatively less influenced by a contrast agent, out of the contrast image data are used as non-contrast image data. Furthermore, the image acquisition part 30 may also obtain time series subtraction image data themselves from a desired medical equipment through the network 3.

The subtraction image generation part 31 has a function to generate subtraction image data by subtraction processing between contrast image data and non-contrast image data.

The PI generation part 32 has a function as a blood flow time identification part and a blood vessel image generation part. The blood flow time identification part is configured to identify a time, such as an inflow time, of a contrast agent signal at every pixel position. Meanwhile, the blood vessel image generation part is configured to generate color image data, according to a color scale, based on the identified times. There are two methods of identifying times in the blood flow time identification part. One is a method of identifying times based on intensities of image signals corresponding to a contrast agent or a blood flow. The other is a method of identifying times based on temporal gradients of the intensities of the image signals.

In the former method, a TDC (time-density curve) of image signals corresponding to a contrast agent or a blood flow is obtained based on at least one of time series contrast image data, time series non-contrast image data and time series subtraction image data. In a case of the time series contrast image data or non-contrast image data of an object, the subtraction image generation part 31 generates subtraction image data by previously performing subtraction between time series contrast image data or non-contrast image data and a non-contrast image.

In the latter method, a time-gradient curve of image signals is obtained based on time series contrast image data, time series non-contrast image data or time series subtraction image data of an object. The time-gradient curve is obtained by calculating a time-density curve at every pixel position based on time series contrast image data, time series non-contrast image data or time series subtraction image data, and subsequently calculating a gradient at every time.

When a time-density curve or a time-gradient curve is obtained for every pixel position, a time at which a concentration or a gradient becomes a specific condition is identified. The blood vessel image generation part converts the time identified for every pixel position into a color pixel value according to a color scale, thereby generates color image data as blood vessel image data.

Hereinafter, color image data generated in the blood vessel image generation part, based on times identified by the blood flow time identification part, are referred to as PI data. Furthermore, an example case where time changes in concentrations of a contrast agent are obtained based on subtraction image data between X-ray contrast image data and X-ray non-contrast image data and PI data having color pixel values corresponding to times at which the concentrations of the contrast agent become a specific condition are generated according to a color scale will be described hereinafter.

In a case of obtaining time changes in image signals corresponding to concentrations of a contrast agent or a blood flow by obtaining subtraction image data using time series contrast CTA image data, time series contrast MRA image data or time series non-contrast MRA image data which are other than X-ray contrast image data, PI data can also be generated in a similar method. Furthermore, also in a case of using a gradient instead of a concentration, PI data can be generated in a similar method, except for obtaining a time-gradient curve instead of a time-density curve to calculate time when the time-gradient curve becomes a specific condition.

Figure 4:
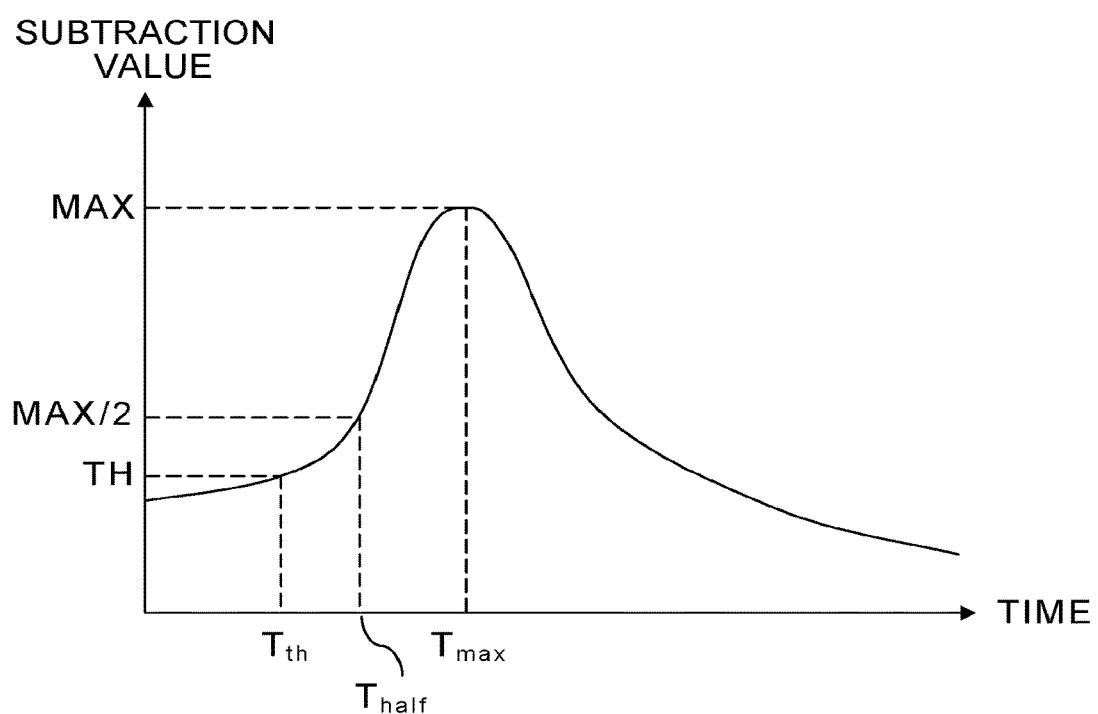
FIG. 4 is a graph showing an example of condition for concentrations of a contrast agent for generating PI data.

FIG. 4 is a graph showing an example of condition for concentrations of a contrast agent for generating PI data.

In FIG. 4, the horizontal axis shows time (time phases) while the vertical axis shows relative intensities (subtraction values) of image signals of subtraction image data sets at a certain pixel position. When intensities of image signals at a certain pixel position are plotted based on time series subtraction image data sets, a TDC showing a change in concentration of a contrast agent can be obtained as a time change in intensities of the image signals.

Consequently, an arrival time, an inflow time or the like of the contrast agent can be obtained for every pixel position based on the TDC influenced by the contrast agent. Specific examples include a method of considering the time $T_{max}$, at which a subtraction value becomes the maximum value, as the arrival time of the contrast agent at the corresponding pixel, a method of considering the time $T_{half}$ at which a subtraction value becomes one half of the maximum value, as the arrival time of the contrast agent at the corresponding pixel, and a method of considering the time $T_{th}$, at which a subtraction value becomes a threshold value TH, as the inflow start time or the like of the contrast agent at the corresponding pixel.

As described above, when time at which a subtraction value becomes a specific condition is obtained for every pixel position, PI data having colors according to time phases, such as arrival time phases or inflow time phases, of a contrast agent can be generated. Note that, a subtraction value at a specific condition may be set to brightness of PI data at the corresponding pixel. When PI data are generated using image data other than subtraction image data, an image signal value at a specific condition or an image signal value whose difference from the previous pixel signal value becomes a specific condition can be set to brightness of PI data at the corresponding pixel similarly.

As an example of the specific condition of a subtraction value, which is set for brightness, the maximum value of the subtraction value at every pixel position or the maximum value of concentration gradient at every pixel position is appropriate.

Figure 5:
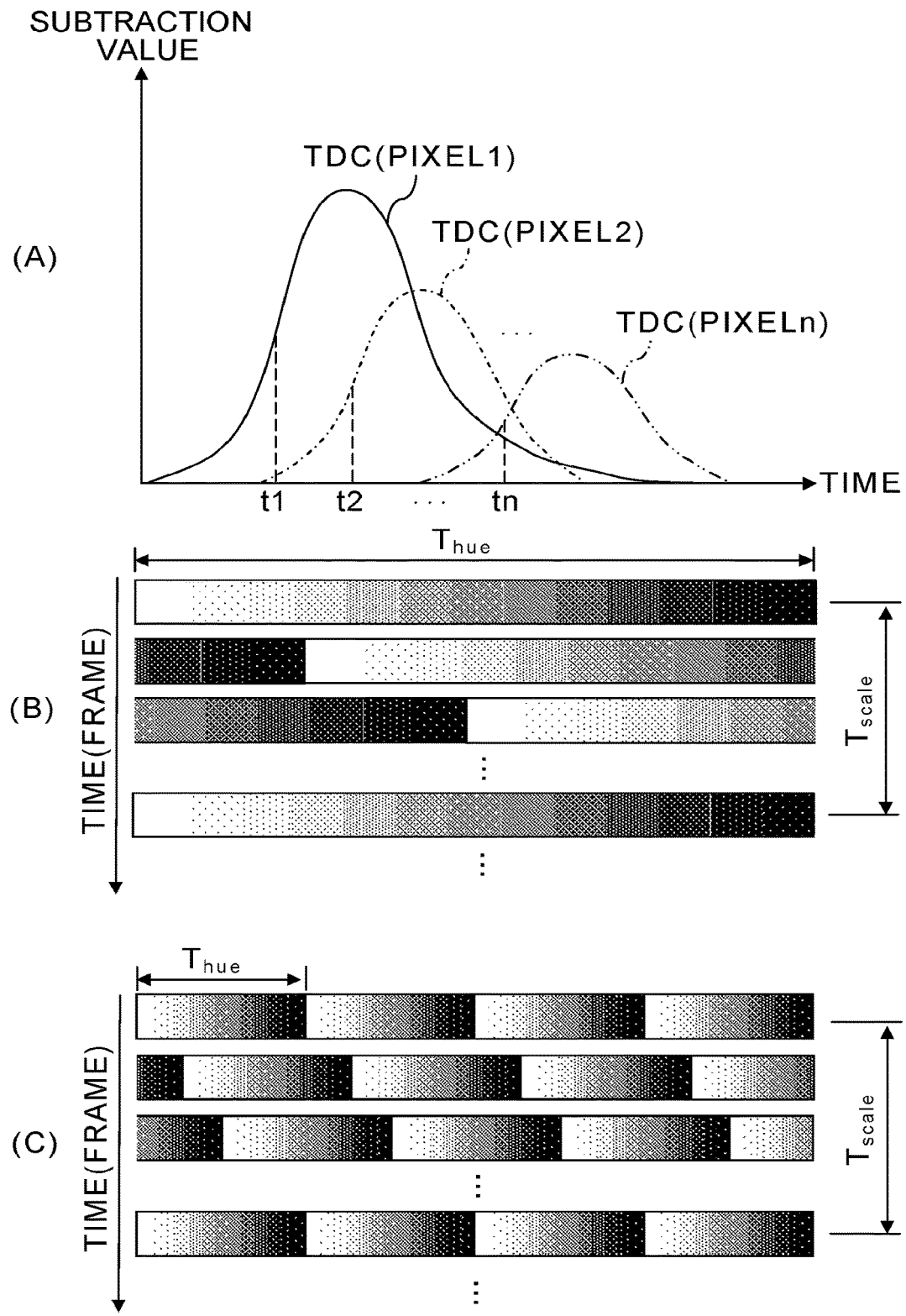
FIG. 5 shows an example of color scales for displaying PI data in color.

FIG. 5 shows an example of color scales for displaying PI data in color.

In the graph of (A) in FIG. 5, the horizontal axis shows time (time phases) while the vertical axis shows image signal values (subtraction values) of subtraction image data sets. That is, the graph of (A) in FIG. 5 shows a time change in subtraction value corresponding to a time change in concentration of a contrast agent. When a time change in subtraction value as shown in FIG. 4 is obtained at respective pixel positions (PIXEL1, PIXEL2, ..., PIXELn), TDCs (TDC(PIXEL1), TDC(PIXEL2), ..., TDC(PIXELn)) influenced by the contrast agent can be obtained as time changes in subtraction values corresponding to the pixel positions (PIXEL1, PIXEL2, ..., PIXELn), as shown in (A) of FIG. 5. Therefore, times t1, t2, ..., tn until concentrations of the contrast agent become a specific condition respectively are also obtained for the respective pixel positions (PIXEL1, PIXEL2, ..., PIXELn). Similarly, times until concentrations of the contrast agent become a specific condition can be obtained for all pixel positions in a region for generating PI data.

On the other hand, (B) of FIG. 5 shows color scales for displaying times, at which time changes in subtraction values become a specific condition, in color. In (B) of FIG. 5, the vertical axis direction shows time. Specifically, times at which time changes in subtraction values become a specific condition can also be displayed as a moving image in color using time series color scales, besides as a still image in color using a single color scale.

When color coding is performed using the color scale at the top of (B) of FIG. 5, for example, a color at the pixel position PIXEL1 become a color phase of the color scale corresponding to the time t1, at which the concentration of the contrast agent at the pixel position PIXEL1 becomes a specific condition, such as one half of the maximum value. Similarly, colors at the pixel positions PIXEL2, ..., PIXELn become color phases of the color scale corresponding to the times t2, ..., tn, at which concentrations of the contrast agent become a specific condition, such as one half of the maximum value, respectively according to the color scale. Therefore, color image data having color phases according to times at which concentrations of the contrast agent become a specific condition, such as one half of the maximum value, can be generated as PI data. Using the above-mentioned PI data for diagnosis allows visual confirmation of arrival time phases or inflow time phases of the contrast agent as differences in color.

Furthermore, by shifting the color scale itself in the time phase direction, i.e., the direction in which the color phase changes, plural color scales of which a change rate in color phase is constant and phases of change in color phase are different can be generated as shown in (B) of FIG. 5. Then, PI data can be generated as a moving image when color coding of the PI data is performed with changing the color scale at a certain time interval.

In this case, the frame rate of the moving PI data becomes the change rate of the color scale. When the color scale is changed to the following color scale, the frame of the moving PI data is changed to the following frame. When the color scale is shifted in the direction, in which the color phase changes, by the length of the color scale, the shifted color scale coincides with the original color scale. Therefore, the moving PI data are moving image data in which colors change periodically at a period $T_{scale}$. In other words, the moving PI data are moving image data which repeatedly play a set of frames of the PI data of which colors are different. Therefore, a loop play of the moving PI data can performed, so that the color scale is shifted sequentially in the direction of the color phase change at the respective pixels of the PI data, until an instruction to stop the playing the moving PI data is input from the input circuit 20.

A period $T_{hue}$ is same with acquisition time range in previous example as shown in (B) of FIG. 5, where color phases change in a period $T_{hue}$ in each color scale. However, as shown in (C) of FIG. 5, it is effective to make the period $T_{hue}$ sufficiently shorter than a time range, that is, a time phase range of time series subtraction image data sets used for generating PI data, from a viewpoint of improving visibility. When the period $T_{hue}$ of the color phase change in the color scale is set short, slight differences in times at which subtraction values at the respective pixel positions becomes a specific condition can be distinguished by differences in color phases. That is, the time resolution by the color phase change can be improved. Therefore, slight differences in arrival time phases of the contrast agent or the like can be visually confirmed by differences in color phases.

When the color scale exemplified in (C) of FIG. 5 is shifted in the direction of the color phase change by the period $T_{hue}$ of the color phase change, the shifted color scale coincides with the original color scale. Therefore, when moving PI data are generated using the color scales exemplified in (C) of FIG. 5, colors of the moving PI data change periodically in the period $T_{hue}$.

Example cases of generating the moving PI data by shifting a color scale itself in the direction of the color phase change are shown in (B) and (C) of FIG. 5. Similarly, moving PI data can also be generated by sequentially shifting the time at which a subtraction value becomes a specific condition, i.e., the time axis, in the time direction by a constant time, instead of shifting the color scale. As a matter of course, both the color scale and the time axis may be shifted. That is, the moving PI data can be generated by shifting the color scale in the direction of the color phase change, relatively to times at which intensities of image signals, such as subtraction values, become a specific condition.

Figure 6:
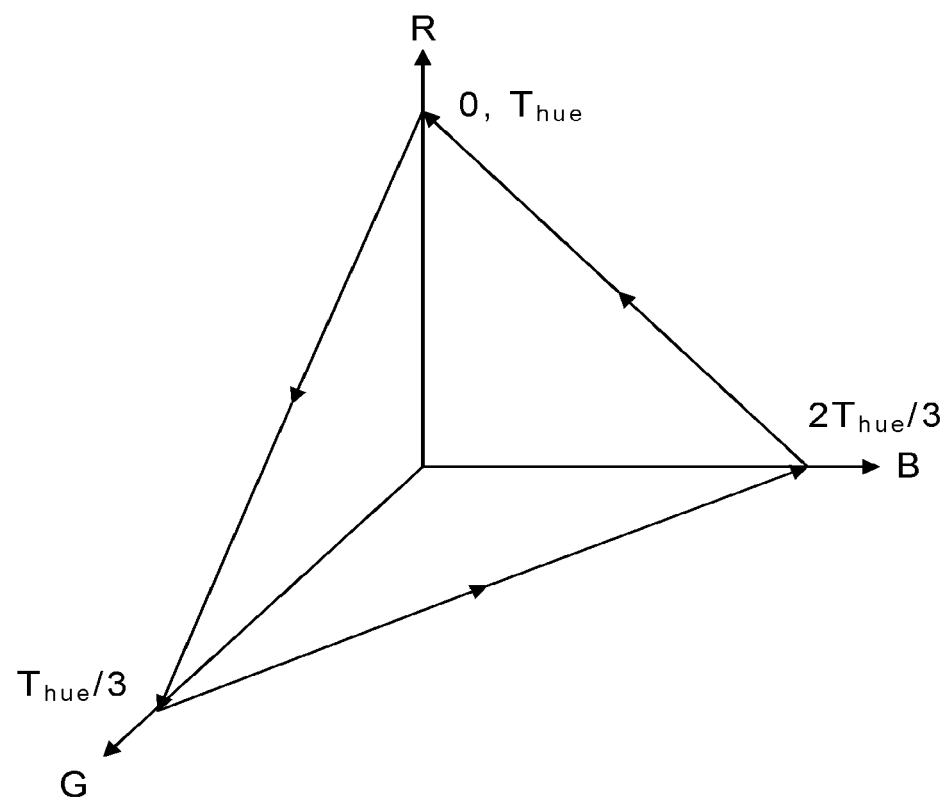
FIG. 6 is a graph showing an example of method of changing a color phase in a color scale.

FIG. 6 is a graph showing an example of method of changing a color phase in a color scale.

The three orthogonal axes in FIG. 6 represent R values, G values, and B values, respectively. The R value, G value, and B value corresponding to each time phase in the period $T_{hue}$ can be determined along the sides of the color triangle, whose vertexes are the maximum value of the R values, the maximum value of the G values, and the maximum value of the B values, as shown in FIG. 6. Specifically, the colors can be arranged so that the G value and the B value become zero and the R value becomes the maximum value when the relative time is zero or $T_{hue}$, the R value and the B value become zero and the G value becomes the maximum value when the relative time is $T_{hue}/3$, and the R value and the G value become zero and the B value becomes the maximum value when the relative time is $2T_{hue}/3$.

When such a color scheme is performed, PI data can be generated so that the color changes from red to blue through green, and then returns to red again as the arrival time phase of a contrast agent or the like becomes late. Note that, the colors between red, green, and blue can be assigned to time phases so that the R value, the G value, and the B value change linearly, for example. Alternatively, the R values, the G values, and the B values may also be assigned to time phases so that the angle of a line segment, which connects the center of the color triangle with a point on the sides, changes linearly.

Therefore, a change in color can be made continuous when moving PI data are generated by shifting a color scale sequentially in the direction of the color phase change, or further when the color phase change in the color scale is repeated in the predetermined period $T_{hue}$ which is shorter than the time range $T_{scale}$. That is, both the first color and the last color of the color phase change become red. Therefore, the change in color can always be made continuous.

As described above, the display processing part 33 can continuously change at least one parameter out of the R value, the G value and the B value between frames of the PI data.

In addition, each color phase in a color scale can also be changed along the color circle in which the whole color phases has been orderly arranged to be a circular ring. That is, the display processing part 33 can also perform a loop play of PI data, until an instruction to stop the loop play is input from the input circuit 20, so that a color at each pixel of the PI data changes along the color circle. In this case, the change in color also can always be made continuous since the first color of the color phase change coincides with the last color of the color phase change.

Next, detailed functions of the display processing part 33 will be described.

The display processing part 33 has a function to perform necessary display processing of desired image data obtained or generated in the image acquisition part 30, the subtraction image generation part 31 or the PI generation part 32. The display processing part 33 also has a function to perform necessary display processing of desired image data stored in the image storage part 43. Furthermore, the display processing part 33 has a function to output the image data after the display processing, to the display 19. In particular, the display processing part 33 has a function as a GUI (graphical user interface) which displays electronic keys, scroll bars or the like for designating image display conditions by operating the input circuit 20, on the display 19, and performs display processing according to the display conditions designated by operating the input circuit 20.

The parallel display processing part 34 has a function to display a subtraction image and a PI in parallel on the display 19. As a matter of course, both subtraction images and PIs can be displayed in parallel as moving images. Specifically, the first moving image obtained as PIs by shifting a color scale and the second moving image consisting of time series subtraction images can be displayed in parallel.

Figure 7:
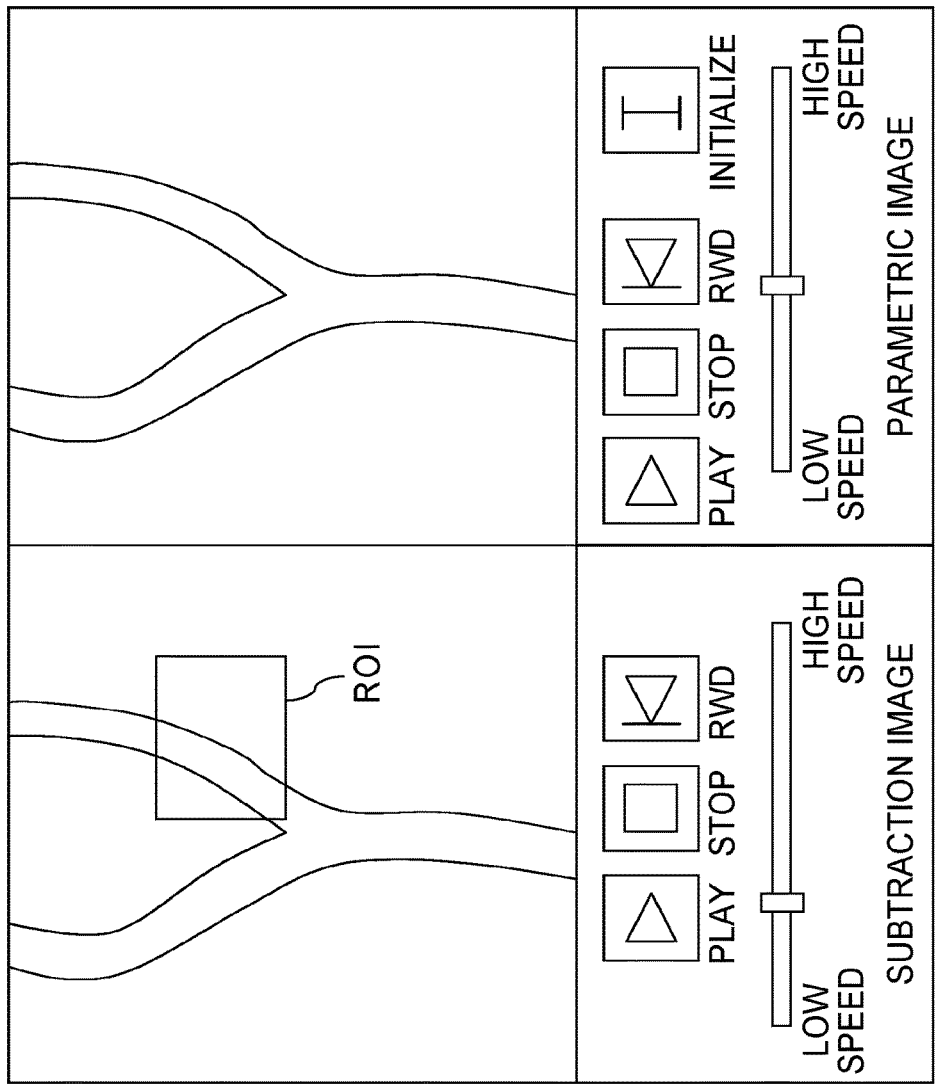
FIG. 7 shows an example of screen on which a subtraction image and a PI have been displayed in parallel.

FIG. 7 shows an example of screen on which a subtraction image and a PI have been displayed in parallel.

As shown in FIG. 7, the subtraction image and the PI can be displayed in parallel. Furthermore, a moving PI as the first moving image and a subtraction moving image as the second moving image can be arranged and played simultaneously. Thereby, a user can perceive a blood flow dynamic state more easily.

When an affine transformation including expansion, reduction, translation and/or rotation has been applied to either a moving PI or a subtraction moving image, the affine transformation synchronization part 35 is configured to synchronously apply the affine transformation to the other. In other words, when an affine transformation is performed for either a moving PI or a subtraction moving image by operating the input circuit 20, the affine transformation synchronization part 35 automatically performs the affine transformation of the other. Thereby, a user can always observe a moving PI and a subtraction moving image with a same enlargement factor from a same observation position. The synchronization function of affine transformation can also be applied when a PI is not a moving image but a still image.

The play/stop instruction part 36 has a function to display widgets (parts of GUI), such as electronic keys, for instructing to play and stop a subtraction moving image and a moving PI by operating the input circuit 20, on the display 19. The play/stop instruction part 36 also has a function to play and stop a subtraction moving image and a moving PI according to instruction information input from the input circuit 20. Each of a subtraction moving image and a moving PI can be played and stopped independently. Therefore, in the example of screen shown in FIG. 7, the PLAY button and the STOP button for a subtraction moving image as well as the PLAY button and the STOP button for a moving PI have been displayed respectively.

Subtraction moving image data consist of time series frames of subtraction image data. Therefore, when a subtraction moving image is played, how a contrast agent flows inside blood vessels with the passage of time is depicted. A subtraction moving image can be stopped at an arbitrary frame, and can be restarted to be played from an arbitrary frame. A RWD (rewind) button may also be prepared so that a subtraction moving image can be played from the initial frame. Furthermore, a repeat function can also be installed so as to automatically restart to play a subtraction moving image from the initial frame in the case that the subtraction moving image has been played up to the last frame.

Meanwhile, moving PI data are generated by shifting a color scale continuously in the direction of the color phase change. Therefore, moving PI data can be continuously displayed on the display 19 until an instruction to stop the moving PI data is input from the input circuit 20. Specifically, frames of the PI data generated by shifting a color scale in the direction of the color phase change can be displayed sequentially on the display 19. Although moving PI data do not change with the passage of time unlike subtraction moving image data, colors appear to move as though blood or a contrast agent was flowing inside blood vessels.

As described above, when a color scale is shifted in the direction of the color phase change, by the period $T_{hue}$ of the color phase change, the shifted color scale coincides with the original color scale. Therefore, a frame of PI corresponding to the initial time $t=t_0$ is same as a frame of PI corresponding to the time $t=t_0+T_{hue}$ after the passage of the period $T_{hue}$ of the color scale change from the initial time $t=t_0$. This relation is similarly satisfied at an arbitrary time t. Therefore, a moving PI repeats a continuous change of color phases at the period $T_{hue}$ until the moving PI is stopped.

The playing speed adjustment part 37 has a function to display widgets, such as scroll bars, for adjusting playing speeds of a subtraction moving image and a moving PI by operating the input circuit 20, on the display 19. The playing speed adjustment part 37 also has a function to adjust the playing speeds of a subtraction moving image and a moving PI, according to instruction information input from the input circuit 20. A playing speed of a subtraction moving image and a playing speed of a moving PI can be adjusted independently from each other. Therefore, in the example shown in FIG. 7, the scroll bar for designating a playing speed of a subtraction moving image and the scroll bar for designating a playing speed of a moving PI have been individually prepared.

A playing speed of a subtraction moving image can be variably set as a frame update rate of time series 2D subtraction images. An acquisition frame rate of the subtraction images can be applied to the default play. Meanwhile, a playing speed of a moving PI can be variably set as at least one of an update rate of a color frame (color scale) and a shift amount in color phase between temporally adjacent color frames (color scales). That is, when an update rate of a color frame is increased, a changing rate of color in a moving PI can be increased. Furthermore, when a shift amount in color phase between temporally adjacent color frames is increased, a changing rate of color in a moving PI can be increased even when an update rate of a color frame is not changed.

Therefore, observation such that overall blood flows are perceived by playing a moving PI at a high speed, and subsequently, local blood flows are perceived by altering the playing speed of the moving PI to slow becomes possible, for example. Furthermore, a moving PI may be able to be displayed frame-by-frame.

The scale phase display part 38 has a function to display a shift amount of a color scale in the direction of the color phase change, on the display 19. A shift amount of a color scale can also be expressed temporally as a phase using the period $T_{hue}$ of the change. In particular, it becomes easy to understand a shift amount of a color scale when the shift amount of the color scale is displayed by a point which moves with corresponding to a unicursal figure of which the starting point is same as the ending point, or by a line segment which connects the moving point with a static point. For example, a shift amount of a color scale can be displayed by a point which moves on the circumference of a unicursal figure of which the starting point is same as the ending point.

Figure 8:
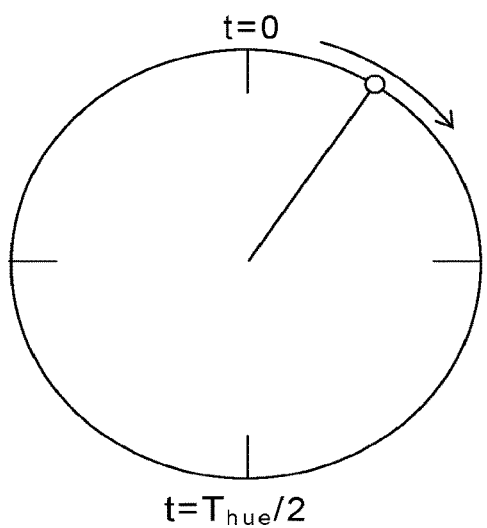
FIG. 8 shows an example of GUI showing phases of a color scale used for displaying a PI.

FIG. 8 shows an example of GUI showing phases of a color scale used for displaying a PI.

As shown in FIG. 8, a shift amount of a color scale can be expressed like a phase by a point which moves on the circumference of a circle, or by a line segment which connects the center of the circle with the point which moves on the circumference of the circle. Specifically, a moving speed of the point which moves on the circumference of the circle can be determined so that the point on the initial position, which starts to move on the circumference of the circle at the time t=0, returns to the initial position at the time $t=T_{hue}$ after passage of the period $T_{hue}$ of the color scale change.

Then, when the initial position of the point at the time t=0 is at the top of the circle as shown in FIG. 8, a position of the point constantly returns to the top of the circle at the timing when the color phase of the color scale has temporally shifted by the integral multiple of the period $T_{hue}$. Furthermore, a position of the point becomes the bottom of the circle at the timing when the color phase of the color scale has shifted by the time derived by adding one half of the period $T_{hue}$ to the integral multiple of the period $T_{hue}$. Therefore, viewing a position of the point on the circumference or the line segment allows perceiving a phase of the color scale easily.

Figure 9:
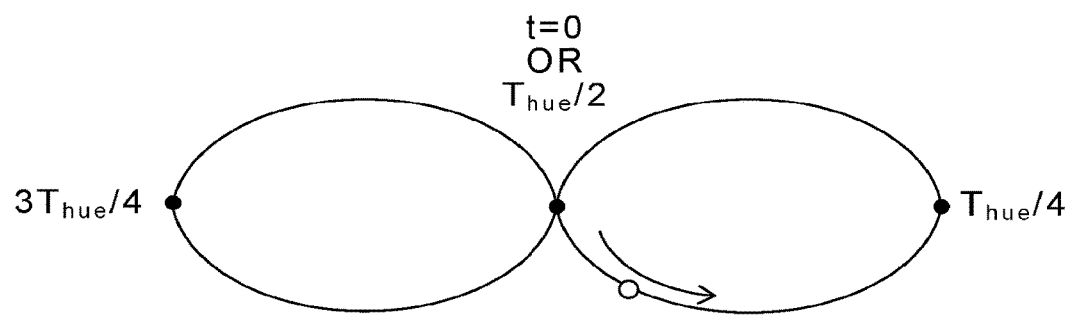
FIG. 9 shows another example of GUI showing phases of a color scale used for displaying a PI.

FIG. 9 shows another example of GUI showing phases of a color scale used for displaying a PI.

As shown in FIG. 9, a shift amount of a color scale can also be expressed like a phase, by a point which moves along the sign ∞ showing the infinity. Specifically, a moving speed of the point which moves on the infinity sign can be determined so that the point on the initial position starts to move at the time t=0 and the point, which passed all the positions on the infinity sign, returns to the initial position at time $t=T_{hue}$ after the passage of the period $T_{hue}$ of the color scale change.

Then, when the initial position of the point at the time t=0 is the intersection position of the curve as shown in FIG. 9, a position of the point returns to the intersection position of the curve at the timing when the color phase of the color scale has temporally shifted by the integral multiple of the period $T_{hue}$ and the timing when the color phase of the color scale has shifted by the time derived by adding one half of the period $T_{hue}$ to the integral multiple of the period $T_{hue}$. Furthermore, a position of the point becomes the right end or the left end of the infinity sign at the timing when the color phase of the color scale has shifted by time derived by adding one quarter or three quarters of the period $T_{hue}$ to the integral multiple of the period $T_{hue}$. Therefore, viewing a position of the point on the infinity sign allows perceiving a phase of the color scale easily.

A phase of a color scale can be expressed not only as the examples shown in FIG. 8 and FIG. 9 but also using a desired figure like a triangle shown in FIG. 6.

The initial scale setting part 39 has a function to set the initial position of a color scale used for playing a moving PI, i.e., the initial color phase pattern of the color scale. In the example shown in FIG. 7, the INITIALIZE button of a color scale has been displayed as a widget of a GUI. When the INITIALIZE button is pressed by operating the input circuit 20 at desired timing during playing of a moving PI, a color scale at the timing when the INITIALIZE button has been pressed can be set to the initial color scale. Specifically, a color scale at desired timing can be set to the initial color scale at the initial time t=0 by pressing the INITIALIZE button of the color scale.

When the clock time at the timing at which the INITIALIZE button of a color scale has been pressed is t=ti in each of the GUIs shown in FIG. 8 and FIG. 9, the initial position of the color scale is set by time conversion processing which gives an offset to the time t, during which the color scale has been changed, by time −ti so that the clock time t=ti becomes the clock time t=0 while the clock time t=ti+$T_{hue}$ becomes the clock time t=$T_{hue}$. Therefore, in each of the GUIs shown in FIG. 8 and FIG. 9, the point is to be displayed on the initial position at the clock time t=ti+n$T_{hue}$, after the passage of n (n=0, 1, 2, . . . ) times the period $T_{hue}$ from the clock time t=ti at which the INITIALIZE button has been pressed.

As described above, a shift amount of a color scale is a relative amount to the time at which an image signal value, such as a subtraction value, becomes a specific condition. Therefore, the initial position of a color scale may also be set by shifting the time at which an image signal value, such as a subtraction value, becomes a specific condition, relative to the color scale.

The scale initialization instruction part 40 has a function to set a color scale, used for the color coding of a moving PI, to the initial color scale. Specifically, when an instruction to return the color scale to the initial color scale has been input to the scale initialization instruction part 40 by operating the input circuit 20 during playing of a moving PI, the scale initialization instruction part 40 is configured to return the color scale to the initial color scale.

In the example shown in FIG. 7, a button to return to the initial frame has been prepared as an electronic button for setting a display condition of a moving PI. Therefore, when the RWD button of a moving PI is pressed by operating the input circuit 20, colors of the moving PI can be returned to the initial colors to restart to play the moving PI.

Therefore, when a user desires to observe a blood flow in a focused region, the user can press the INITIALIZE button of a color scale at the timing, at which a color at the most upstream position in the focused region becomes easily visible red, and subsequently press the RWD button of a moving PI to play the moving PI, for example. Then, the blood flow in the focused region can be observed as a movement of red.

The playing period designation part 41 has a function to automatically designate a playing period of a subtraction moving image appropriate for a target region designated by operating the input circuit 20. That is, a subtraction moving image consisting of time series 2D subtraction images in a predetermined period can be played instead of displaying all the time series frames of 2D subtraction images.

A target region for designating a playing period of a subtraction moving image can be designated by using the subtraction moving image or a moving PI as a reference image. In the example shown in FIG. 7, a ROI has been set in the display area of a subtraction moving image, as a target region for designating a playing period of the subtraction moving image.

A playing period of a subtraction moving image can be determined based on the minimum value and the maximum value of times at which subtraction values inside a target region become a specific condition, such as the maximum values or the half values, respectively. Specifically, a playing period of a subtraction moving image can be set so that the minimum value and the maximum value of times at which subtraction values inside a target region become a specific condition are covered. Then, the playing period of the subtraction moving image can be set so that timing when a contrast agent flows into the target region earliest and timing when the contrast agent arrives at the target region latest are covered. Therefore, a subtraction moving image in a period when the contrast agent flows into and arrives at the target region can be played selectively.

Figure 10:
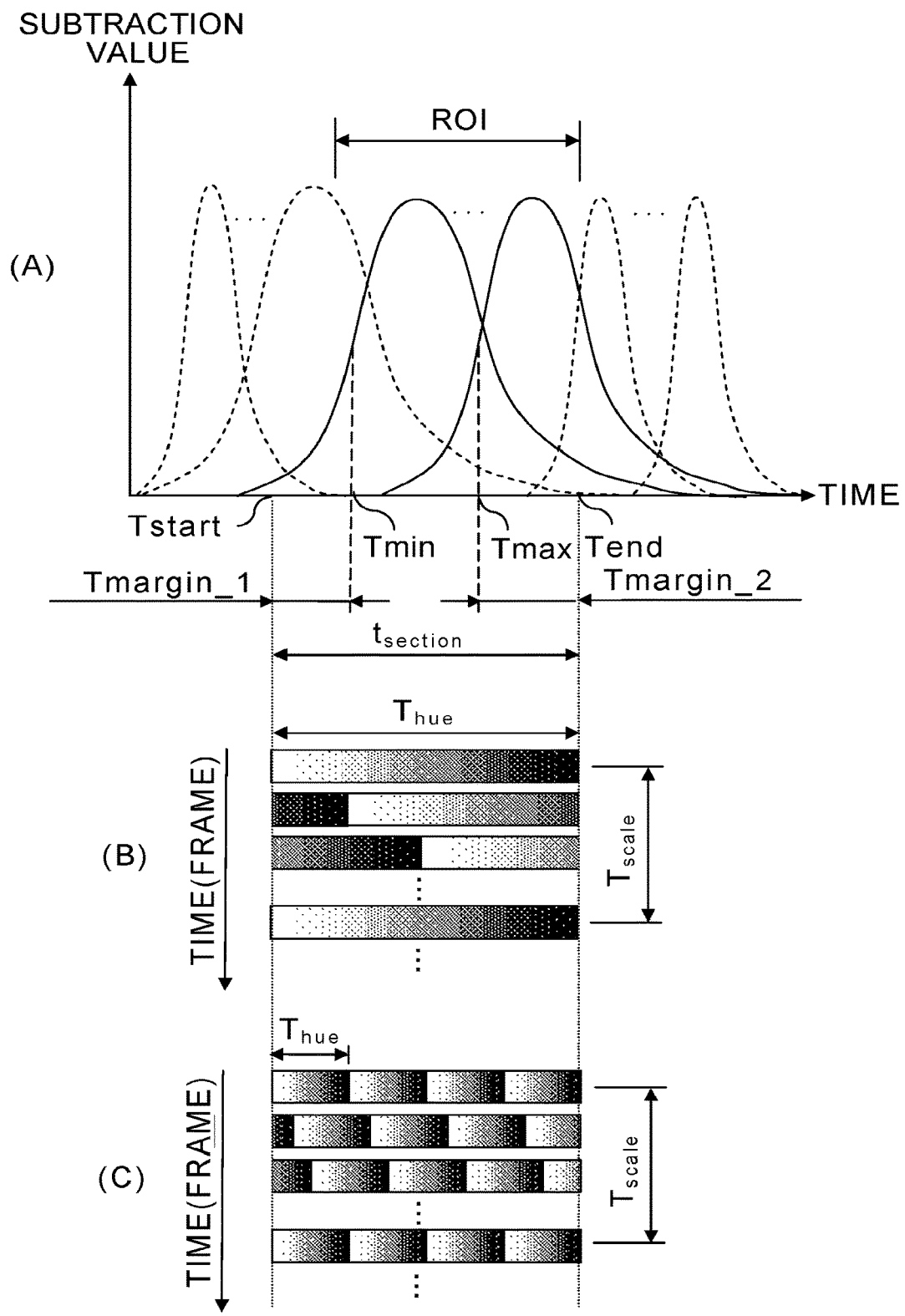
FIG. 10 explains a method for designating a playing period of a subtraction moving image, appropriate for a target region.

FIG. 10 explains a method for designating a playing period of a subtraction moving image, appropriate for a target region.

In the graph of (A) of FIG. 10, the horizontal axis shows time (time phases) while the vertical axis shows image signal values (subtraction values) of subtraction image data sets. As shown in (A) of FIG. 10, the minimum value Tmin and the maximum value Tmax of times when subtraction values become a specific condition can be specified with limiting to time changes in the subtraction values at respective pixel positions in the ROI set as a target region.

Then, a period $t_{section}$ (Tstart=Tmin−Tmargin_1≤$t_{section}$≤Tend=Tmax+Tmargin_2) can be set to a playing period during which time series frames of 2D subtraction images are played as a subtraction moving image. The time Tmin−Tmargin_1 obtained by subtracting the first margin time Tmargin_1 from the minimum value Tmin of times, at which the subtraction values in the ROI become a specific condition, is set as the start time Tstart of the period $t_{section}$. The time Tmax+Tmargin_2 obtained by adding the second margin time Tmargin_2 to the maximum value Tmax of the times is set as the end time Tend of the period $t_{section}$.

The first margin time Tmargin_1 and the second margin time Tmargin_2 can previously be determined empirically and arbitrarily. For example, the first margin time Tmargin_1 for the minimum value Tmin of times corresponding to inflow times of a contrast agent can be practically determined close to zero while the second margin time Tmargin_2 for the maximum value Tmax of times corresponding to inflow times of a contrast agent can be practically determined to approximately one second. On the other hand, the first margin time Tmargin_1 for the minimum value Tmin of times when subtraction values become the maximum values can be practically determined to approximately one second while the second margin time Tmargin_2 for the maximum value Tmax of times when subtraction values become the maximum value can be practically determined close to zero. Further, the first margin time Tmargin_1 for the minimum value Tmin of times when subtraction values become the half values of the maximum values can be practically determined to approximately 500 ms while the second margin time Tmargin_2 for the maximum value Tmax of times when subtraction values become the half values of the maximum values can be practically determined to approximately 500 ms.

Alternatively, each of the first margin time Tmargin_1 and the second margin time Tmargin_2 can also be set to a sufficiently long time not less than one second. In that case, setting the first margin time Tmargin_1 to a time longer than the second margin time Tmargin_2 can avoid lack of frames which should be displayed for helpfulness.

Note that, PI data may be generated only using time series frames of subtraction image data included in a playing period. Each of (B) and (C) of FIG. 10 shows an example of color scales used in the case of generating PI data only using time series frames of subtraction image data included in a playing period corresponding to the ROI.

When still PI data or moving PI data are generated using the color scales exemplified in (B) or (C) of FIG. 10, a period from the minimum value to the maximum value of times which are pixel values of the PI data becomes short. Therefore, even a slight time difference can be displayed as a difference in color. That is, it becomes possible to visually recognize a slight difference in inflow time or arrival time of the contrast agent in the ROI, easily as a difference in color. In this case, PI data may also be generated for only inside a region same as the target region set as the ROI on the subtraction moving image.

The color synchronization part 42 has a function to synchronize colors between two kinds of moving PIs or still PIs, in which a same blood vessel has been depicted, when the PIs are displayed in parallel. Example cases of generating two kinds of PIs, in which a same blood vessel has been depicted, include: a case where blood vessels have been imaged almost simultaneously from different directions using the biplane type of X-ray diagnostic apparatus 6 as shown in FIG. 2; and a case where blood vessels have been imaged at different times, such as before and after a surgery.

When blood vessels have been imaged from different directions using the biplane type of X-ray diagnostic apparatus 6, time series subtraction image data sets in the F side and time series subtraction image data sets in the L side can be obtained. Therefore, PI data in the F side and PI data in the L side can be individually generated.

Thus, when two frames of PI data corresponding to different imaging directions have been generated, synchronous processing for displaying positions of blood vessels, corresponding between the two frames of the PI data, in a same color can be performed. The two frames of the PI data after the synchronous processing are not only displayed as still images on the display 19, but can be continuously displayed as moving images on the display 19.

The synchronous processing for displaying positions of blood vessels, corresponding between two frames of PI data in the F side and the L side obtained using the biplane type of X-ray diagnostic apparatus 6, in a same color, can be performed by canceling a difference in data acquisition time between X-ray contrast image data in the F side and X-ray contrast image data in the L side.

Figure 11:
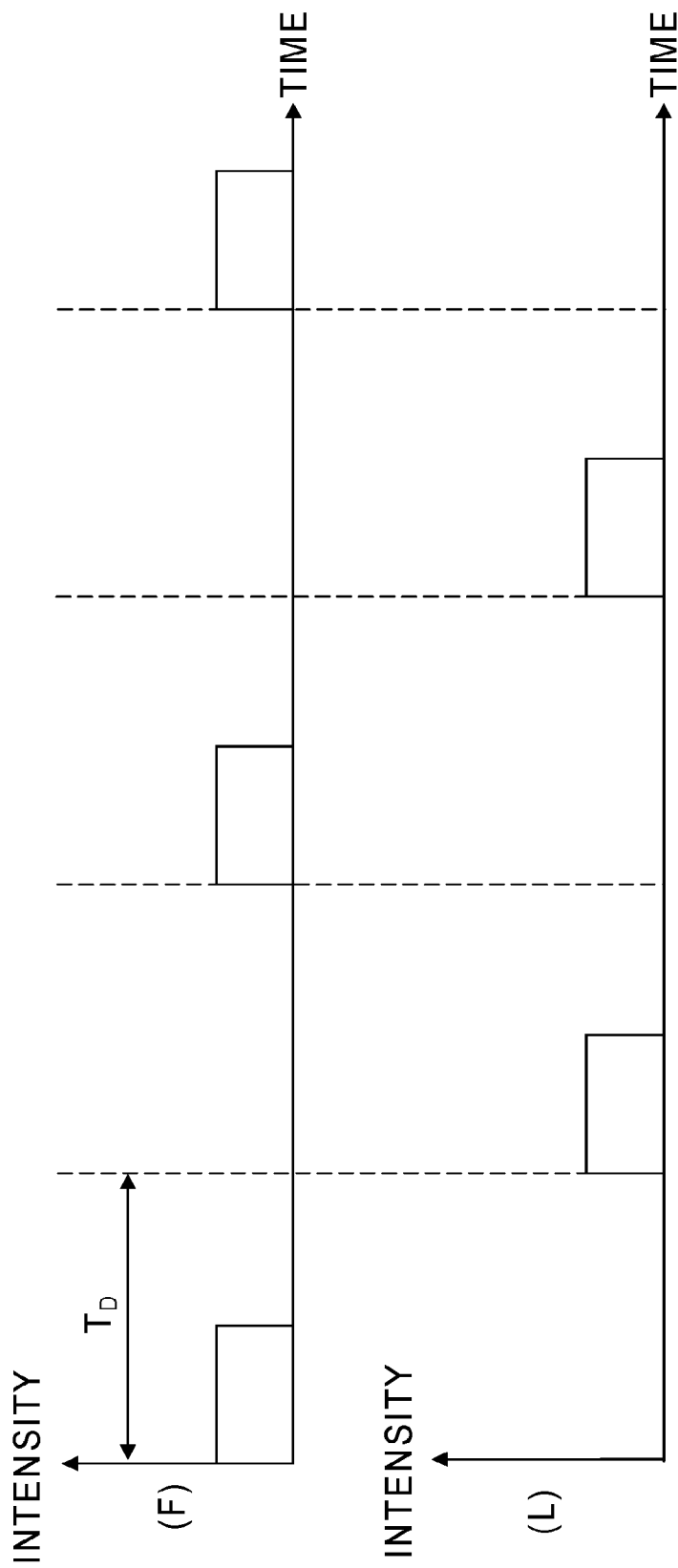
FIG. 11 shows graphs for explaining an example of processing to cancel a difference in data acquisition time between X-ray contrast image data in the F side and X-ray contrast image data in the L side.

FIG. 11 shows graphs for explaining an example of processing to cancel a difference in data acquisition time between X-ray contrast image data in the F side and X-ray contrast image data in the L side.

In the graphs of FIG. 11, the horizontal axes show time while the vertical axes show intensities of control pulses which are output to high voltage generators for the F side and the L side included in the control system 9 of the X-ray diagnostic apparatus 6. (F) of FIG. 11 shows control pulses which are output to the high voltage generator for the F side while (L) of FIG. 11 shows control pulses which are output to the high voltage generator for the L side.

As shown in FIG. 11, control pulses are output alternately to the high voltage generator for the F side and the high voltage generator for the L side. When a high voltage is applied to the first imaging system 8A for the F side from the high voltage generator for the F side according to a control pulse, an X-ray is exposed from the first imaging system 8A for a period according to a length of the control pulse. When the exposure of X-ray ends, the first X-ray detector 13A for the F side detects the X-ray signals for a certain period.

When the detection of the X-ray by the first X-ray detector 13A for the F side ends, a control pulse is output to the high voltage generator for the L side. Then, similarly to the F side, an X-ray is exposed from the second imaging system 8B by applying a high voltage to the second imaging system 8B for the L side from the high voltage generator for the L side. When the exposure of X-ray ends, the second X-ray detector 13B for the L side detects the X-ray signals.

As described above, a time difference $T_D$ exists between the output timing of a control pulse to the high voltage generator for the F side and the output timing of a control pulse to the high voltage generator for the L side. Thus, at least one of PI data in the F side and PI data in the L side can be corrected so that the time difference $T_D$ is canceled. Specifically, synchronous processing of color scales has only to be performed so as to convert a color scale, used for the color coding of the PI data in the L side, to a color scale obtained by shifting a color scale, used for the color coding of the PI data in the F side, by the time difference $T_D$ in the change direction of phase. The similar applies to moving PIs.

As a more specific example, when a pair of X-ray contrast image data in the F side and X-ray contrast image data in the L side are acquired at 10 pps (pair per second), the time difference $T_D$ between the output timing of each control pulse to the high voltage generator for the F side and the output timing of each control pulse to the high voltage generator for the L side is 50 ms. Therefore, a color scale obtained by shifting a color scale for PIs in the F side by 50 ms in the change direction of phase has only to be set as a color scale for PIs in the L side. Then, a moving PI in the L side and a moving PI in the F side, in which positions of a same blood vessel are displayed in a same color, can be displayed in parallel by changing the color scale for PIs in the F side and the color scale for PIs in the L side to color scales, which have been shifted by a same shift amount in the change direction of phase, respectively at a same changing rate.

Note that, the time difference $T_D$ between PI data in the F side and PI data in the L side may be canceled by a relative shift of the time axes for showing time changes in subtraction values, instead of a relative shift between a color scale for the PI data in the F side and a color scale for the PI data in the L side. In this case, same color scales can be used in order to synchronously display a moving PI in the L side and a moving PI in the F side.

Figure 12:
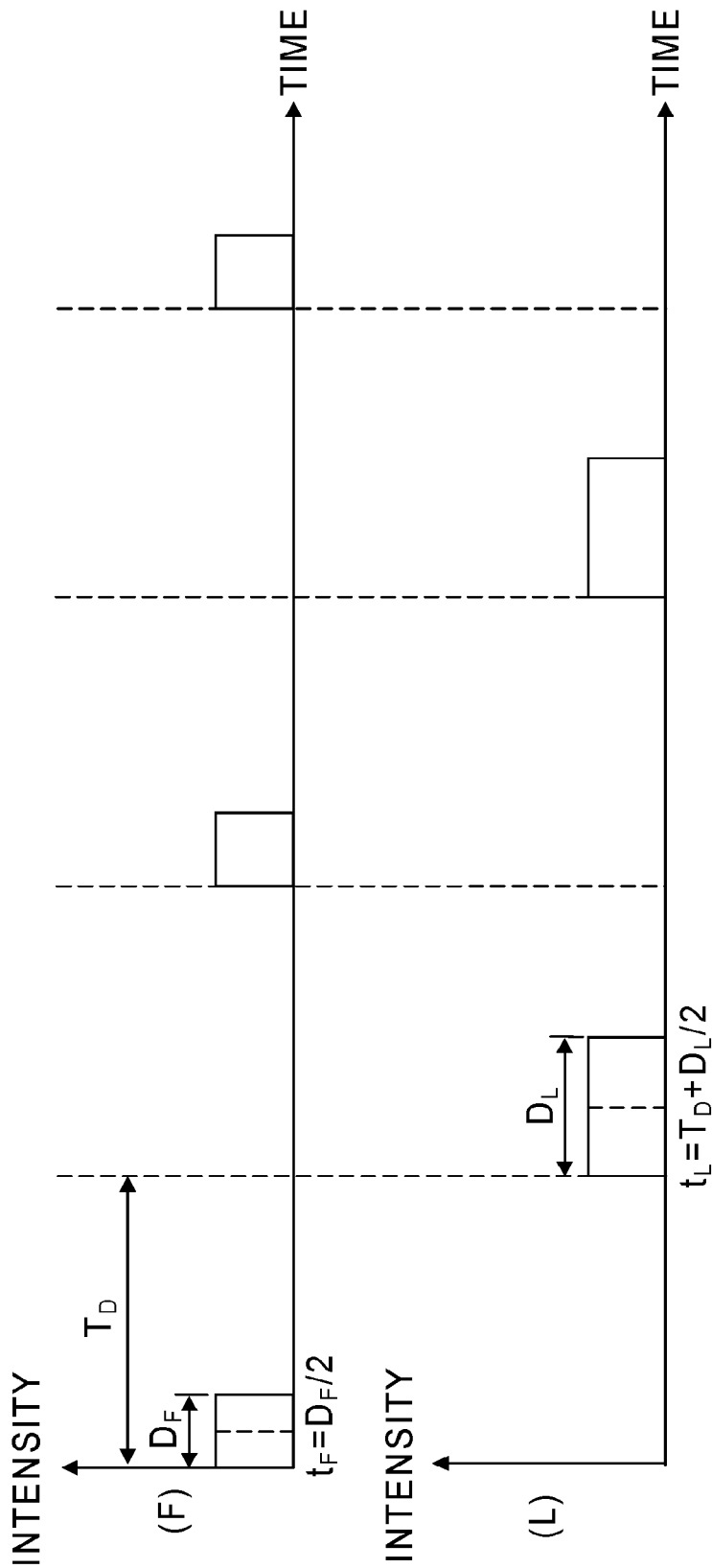
FIG. 12 shows graphs for explaining another example of processing to cancel a difference in data acquisition time between X-ray contrast image data in the F side and X-ray contrast image data in the L side.

FIG. 12 shows graphs for explaining another example of processing to cancel a difference in data acquisition time between X-ray contrast image data in the F side and X-ray contrast image data in the L side.

In the respective graphs of FIG. 12, the horizontal axes show time while the vertical axes show intensities of control pulses which are output to high voltage generators for the F side and the L side included in the control system 9 of the X-ray diagnostic apparatus 6. (F) of FIG. 12 shows control pulses which are output to the high voltage generator for the F side while (L) of FIG. 12 shows control pulses which are output to the high voltage generator for the L side.

In the example shown in FIG. 11, the case where a difference between a pulse width of each control pulse which is output to the high voltage generator for the F side and a pulse width of each control pulse which is output to the high voltage generator for the L side is negligible has been described. Meanwhile, there is a case where the difference between the pulse widths is non-negligible, as exemplified in FIG. 12.

Specifically, when the pulse width of each control pulse which is output to the high voltage generator for the F side is $D_F$ while the pulse width of each control pulse which is output to the high voltage generator for the L side is $D_L$, the center time $t_F$ of the control pulse output to the high voltage generator for the F side becomes $t_F=D_F/2$ when the initial time is t=0. Meanwhile, the center time $t_L$ of the control pulse output to the high voltage generator for the L side becomes $t_L=T_D+D_L/2$ when a time difference between the output timing of the control pulse to the high voltage generator for the F side and the output timing of the control pulse to the high voltage generator for the L side is $T_D$. Therefore, a time difference between the center time $t_F$ of the control pulse output to the high voltage generator for the F side and the center time $t_L$ of the control pulse output to the high voltage generator for the L side is $t_L-t_F=T_D+D_L/2-D_F/2$.

Accordingly, when a relative shift amount between a color scale for PI data in the F side and a color scale for PI data in the L side is set to a color phase variation corresponding to the time difference $t_L-t_F=T_D+D_L/2-D_F/2$, the time difference $t_L-t_F=T_D+D_L/2-D_F/2$ can be canceled. Similarly in this case, the time difference $t_L-t_F=T_D+D_L/2-D_F/2$ can be canceled by a relative shift of the time axes for showing time changes in subtraction values, instead of a relative shift between the color scales.

As a more specific example, when an acquisition rate of a pair of X-ray contrast image data in the F side and X-ray contrast image data in the L side is 10 pps, the pulse width of each control pulse which is output to the high voltage generator for the F side is $D_F=10$ ms, and the pulse width of each control pulse which is output to the high voltage generator for the L side is $D_L=20$ ms, the time difference $T_D$ between the rises of the control pulses is 50 ms. Therefore, the center time of the control pulse output to the high voltage generator for the F side becomes $t_F=5$ ms while the center time of the control pulse output to the high voltage generator for the L side becomes $t_L=60$ ms.

Accordingly, two color scales, which have been shifted relatively by a color phase variation corresponding to $t_L-t_F=55$ ms, have only to set as a color scale for PI data in the F side and a color scale for PI data in the L side, respectively.

As described above, performing the synchronous processing of colors between PI data in the F side and PI data in the L side allows visual confirmation of arrival timings of a contrast agent, from both the F side and the L side, as the same color phase changes. Furthermore, a user can also easily perceive whether a blood vessel depicted on a PI in the F side and a blood vessel depicted on a PI in the L side are the same. In particular, the degree of coincidence of colors between PI data in the F side and PI data in the L side can be further improved by performing the synchronous processing of colors with considering a difference between exposure times of X-rays as described in FIG. 12.

Another example case of generating two kinds of PIs, which may be targets of the synchronous processing of colors, is a case of generating two PI data sets corresponding to different imaging times, such as before and after a treatment, as described above. Specifically, when subtraction image data are obtained before and after a treatment or the like, two PI data sets can be generated independently, based on the two sets of time series frames of subtraction image data.

In this case, catheter positions to inject contrast media and flow velocities of the contrast agent could be different between imagings. Thus, synchronous processing for displaying two points, which have been designated directly or indirectly to two PI data sets respectively, in a same color can be performed. Each of the two PI data sets after the synchronous processing are not only displayed as a still image on the display 19, but can be continuously displayed as a moving image on the display 19.

Figure 13:
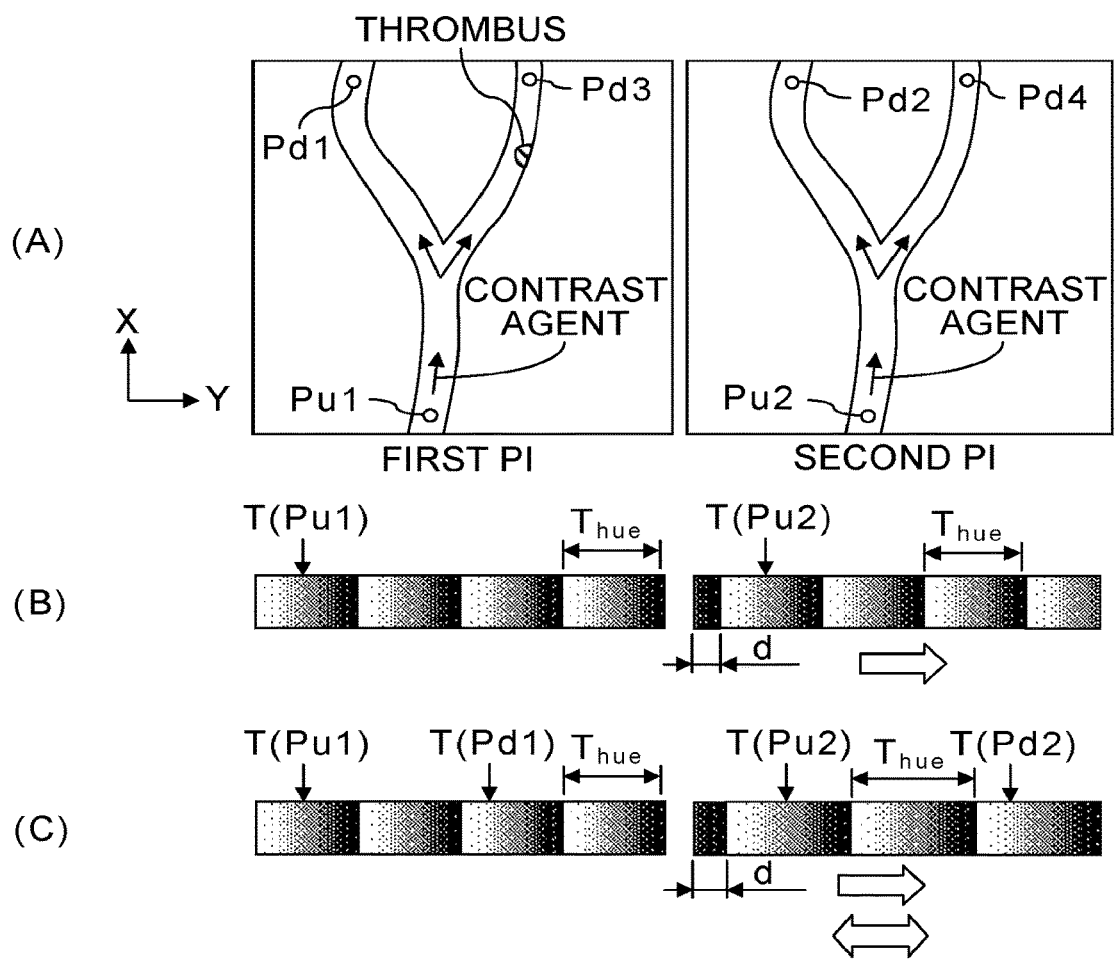
FIG. 13 explains a method of color synchronous processing of moving PIs corresponding to different imaging times.

FIG. 13 explains a method of color synchronous processing of moving PIs corresponding to different imaging times.

(A) of FIG. 13 shows an example of displaying the first PI before a treatment in which a thrombus exists and the second PI after the treatment in which the thrombus has been removed, in parallel. (B) of FIG. 13 shows an example of the initial color scale after the synchronous processing of colors. (C) of FIG. 13 shows another example of the initial color scale after the synchronous processing of colors.

As shown in (A) of FIG. 13, the first position Pu1 can be directly designated on the first PI before the treatment, by operating the input circuit 20, for example. Alternatively, the first position Pu1 may also be indirectly designated on the first PI before the treatment with referring to the first subtraction image before the treatment. Similarly, the second position Pu2, which can be considered anatomically same as the first position Pu1, can be directly designated on the second PI after the treatment, by operating the input circuit 20. Alternatively, the second position Pu2 may also be indirectly designated on the second PI after the treatment, with referring to the second subtraction image after the treatment.

When the first position Pu1 does not change before and after the treatment, it is desirable to display the first position Pu1 on the first PI and the second position Pu2 on the second PI corresponding to the first position Pu1, in a same color. Thus, synchronous processing of colors to shift a color scale for the first PI and a color scale for the second PI relatively by a shift amount d in the direction of the color phase change can be performed as shown in (B) of FIG. 13. Consequently, a color phase corresponding to the time T(Pu1) at which a subtraction value becomes a specific condition at the first position Pu1 on the first PI becomes same as a color phase corresponding to the time T(Pu2) at which a subtraction value becomes the specific condition at the second position Pu2 on the second PI.

Thereby, even when the time T(Pu1) at which a subtraction value becomes a specific condition at the first position Pu1 on the first PI is different from the time T(Pu2) at which a subtraction value becomes the specific condition at the second position Pu2 on the second PI, the time T(Pu1) and the time T(Pu2) can be displayed with a same color phase. That is, a same position of a blood vessel can be displayed on the first PI and the second PI in a same color. This is also similar in the case of displaying the first PI and the second PI as moving images, respectively. Specifically, the first PI and the second PI can be played with synchronizing colors at least between the first position Pu1 on the first PI and the second position Pu2 on the second PI.

A zero-order correction for only moving the two color scales relatively in parallel, in the direction of the color phase change, without changing the period $T_{hue}$ of the color phase change, as shown in (B) of FIG. 13, is useful when positions of a catheter which injects the contrast agent are different between the time of acquiring the first subtraction images and the time of acquiring the second subtraction images.

By contrast, when flow velocities of blood and a contrast agent differ between the time of acquiring the first subtraction images and the time of acquiring the second subtraction images, to a non-negligible extent, colors between the first PI and the second PI cannot coincide completely by only designating one point. Accordingly, other points which can be considered anatomically same can be further designated. The other points which can be considered anatomically same can also be directly designated on PIs or indirectly designated on the PIs with referring to subtraction images.

Then, processing which shifts, expands and contracts a color scale relatively to the time at which a subtraction value becomes a specific condition can be performed as synchronous processing so that the other two points designated directly or indirectly on two frames of PI data respectively are further displayed in a same color.

As a specific example, the third position Pd1 can be directly designated on the first PI before the treatment, by operating the input circuit 20, as shown in (A) of FIG. 13. Alternatively, the third position Pd1 may also be indirectly designated on the first PI before the treatment with referring to the first subtraction image before the treatment. Similarly, the fourth position Pd2, which can be considered anatomically same as the third position Pd1, can be directly designated on the second PI after the treatment, by operating the input circuit 20. Alternatively, the fourth position Pd2 may also be indirectly designated on the second PI after the treatment with referring to the second subtraction image after the treatment.

Then, synchronous processing of colors which shifts, expands and contracts the color scale for the first PI and the color scale for the second PI relatively in the direction of the color phase change can be performed as shown in (C) of FIG. 13 so that a color phase corresponding to the time T(Pu1), at which the subtraction value becomes the specific condition at the first position Pu1 on the first PI, becomes same as a color phase corresponding to the time T(Pu2), at which the subtraction value becomes the specific condition at the second position Pu2 on the second PI while a color phase corresponding to time T(Pd1), at which a subtraction value becomes the specific condition at the third position Pd1 on the first PI, becomes same as a color phase corresponding to a time T(Pd2), at which a subtraction value becomes the specific condition at the fourth position Pd2 on the second PI. That is, a linear correction of color scales which not only shifts the color scale for the first PI and the color scale for the second PI relatively, but expands and contracts the color scale for the first PI and the color scale for the second PI relatively can be performed so that color phases of the first PI and color phases of the second PI coincide at two positions which can be considered anatomically same.

Such correction of color scales can correct the non-coincidence of colors between the first PI and the second PI, resulting from differences in flow velocities of blood and the contrast agent. Specifically, positions of blood vessels which are not influenced by a treatment, like a pair of the first position Pu1 and the second position Pu2, and a pair of the third position Pd1 and the fourth position Pd2, can be synchronously displayed in same colors. Meanwhile, positions of blood vessels which are influenced by a treatment, like the fifth position Pd3 and the sixth position Pd4 in the downstream side of a thrombus, can be displayed in colors according to arrival time phases of a contrast agent so that effects of the treatment can be confirmed. Thus, synchronous processing of colors allows easily confirming a change in blood flow before and after a procedure, as a difference in color.

This is similarly applied to the case of displaying each of the first PI and the second PI as a moving image. Specifically, even in the case that an expansion and contraction correction of the color scales has been performed, a playing speed of the first PI can be set to be same as a playing speed of the second PI since a playing speed of a moving image can be set as a changing rate of a color scale, independently of the period $T_{hue}$ of phase change.

Note that, a relative shift, expansion and contraction of time axes for expressing time changes of subtraction values may be performed instead of shifting, expanding and contracting the color scales. In that case, synchronous processing of colors can be performed without shifting, expanding and contracting the color scales. That is, synchronous processing of colors can be performed using the same color scales, by processing which shifts, expands and contracts at least one of two time axes relatively to times at which subtraction values become a specific condition, as described above.

When imaging in the F side and imaging in the L side have been performed at different times using the biplane type of X-ray diagnostic apparatus 6, both of the synchronous processing of colors between a PI in the F side and a PI in the L side and the synchronous processing of colors between PIs corresponding to the different imaging times can be performed.

(Operation and Action)

Next, an operation and action of the medical image processing apparatus 1 will be described. An example case where the X-ray diagnostic apparatus 6 acquires X-ray contrast image data of an object, and the medical image processing apparatus 1 displays a subtraction moving image and a moving PI in parallel will be described here.

Figure 14:
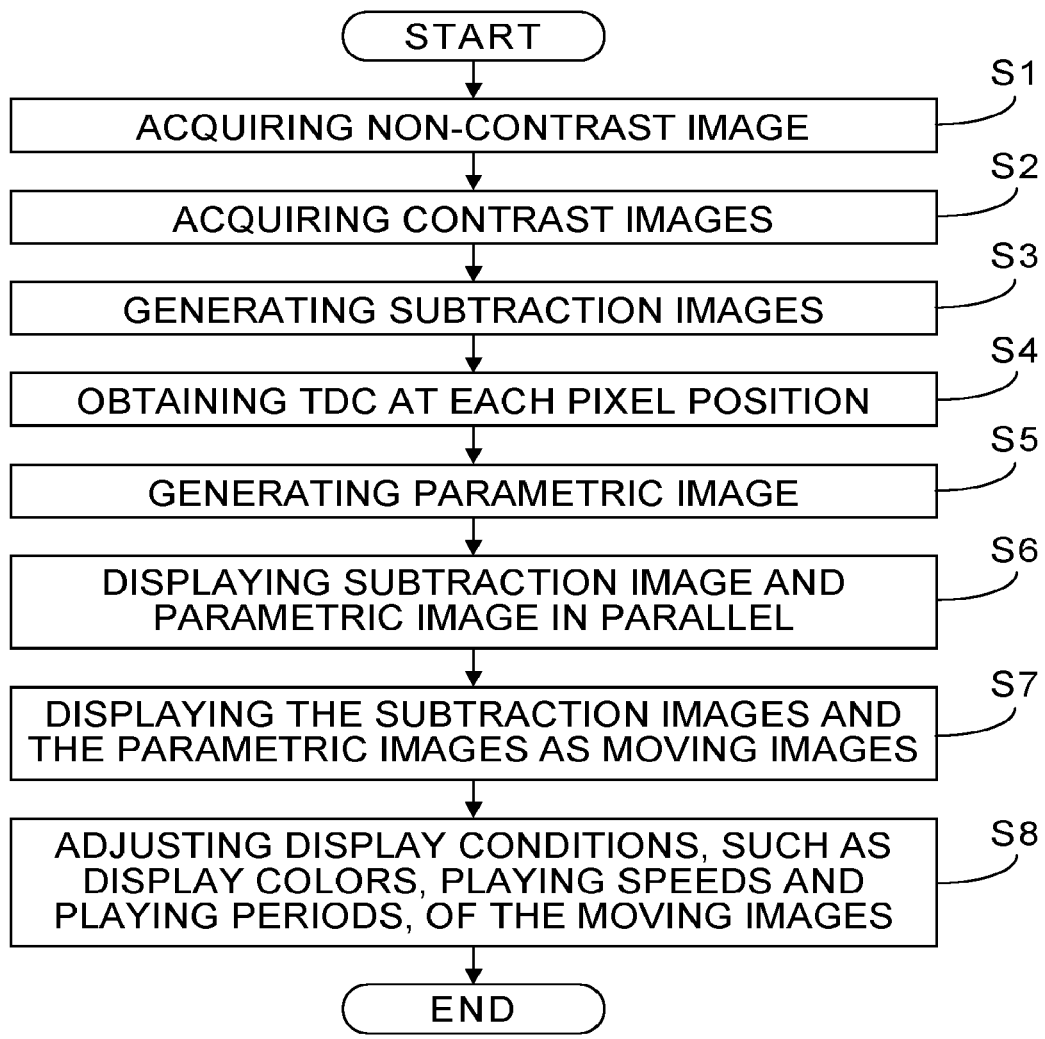
FIG. 14 is a flow chart showing a flow of an operation and processing of the X-ray diagnostic apparatus and the medical image processing apparatus shown in FIG. 1.

FIG. 14 is a flow chart showing a flow of an operation and processing of the X-ray diagnostic apparatus 6 and the medical image processing apparatus 1 shown in FIG. 1.

Firstly, in step S1, X-ray image data of the object before injecting a contrast agent are acquired as non-contrast image data by the X-ray diagnostic apparatus 6. Next, in step S2, the contrast agent is injected into the object, and time series X-ray contrast image data of the object are acquired sequentially by the X-ray diagnostic apparatus 6.

Next, in step S3, the time series frames of X-ray contrast image data are sequentially subtracted from the non-contrast image data acquired without contrast agent, in the subtraction image generation part 31 of the medical image processing apparatus 1 built in the X-ray diagnostic apparatus 6 or coupled to the X-ray diagnostic apparatus 6. Thereby, time series subtraction image data sets of the object are generated.

Next, in step S4, the PI generation part 32 of the medical image processing apparatus 1 obtains a TDC due to influence of the contrast agent at every pixel position, as a time change in subtraction value at every pixel position, as exemplified in (A) of FIG. 5, based on the time series subtraction image data sets. Next, in step S5, the PI generation part 32 generates PI data, having color pixel values according to times until subtraction values showing concentrations of the contrast agent become a specific condition, based on the TDCs due to the influence of the contrast agent.

Next, in step S6, the parallel display processing part 34 displays the PI data and typical 2D subtraction image data, such as the initial frame of subtraction image data, out of the time series frames of subtraction image data used for generating the PI data, in parallel on the display 19. Thereby, a user can observe the subtraction image and the PI through a GUI as exemplified in FIG. 7. Furthermore, the subtraction image and the PI can be displayed under a variety of display conditions.

For example, when the PLAY button of subtraction images and the PLAY button of PIs are pressed, the subtraction images and the PIs are displayed as moving images respectively, by display processing by the play/stop instruction part 36, in step S7. Thereby, the user can confirm whole blood flows in an imaging region, by observing the moving PI. Furthermore, a temporal relationship of earlier and later time phases of blood flows can be perceived by observing the subtraction moving image.

Next, in step S8, the user can adjust display conditions, such as display colors, playing speeds and playing periods of the subtraction moving image and the moving PI, as necessary. As a specific example, when an affine transformation is applied to one of the subtraction moving image or the moving PI by operating the input circuit 20, the similar affine transformation is also applied to the other by the synchronous processing in the affine transformation synchronization part 35. Thereby, the user can observe the subtraction moving image and the moving PI, synchronized at a desired observation position and a desired enlargement factor.

The respective playing speeds of the moving PI and the subtraction moving image can be adjusted by giving instruction information from the input circuit 20 to the playing speed adjustment part 37. Therefore, comprehensive blood flows can be perceived by observing the moving PI played at the initial playing speed, for example. After that, the playing speed of the moving PI may be reduced in order to confirm a local blood flow. Alternatively, the moving PI may be displayed frame-by-frame in order to confirm a local blood flow. After perceiving blood flows by observing the moving PI, it can be confirmed whether the prehension of the blood flows is correct, by playing the subtraction moving image at a slow playing speed or displaying the subtraction moving image frame-by-frame. The playing speed of the moving PI and a phase of the color scale can be displayed on the display 19, by the scale phase display part 38, using a variety of GUIs as exemplified in FIG. 8 or FIG. 9.

In addition, a ROI can be designated on the subtraction moving image or the moving PI by operating the input circuit 20. In this case, a subtraction moving image in a period during which the contrast agent flows in and arrives at the ROI can be selectively played by display processing in the playing period designation part 41.

On the other hand, the INITIALIZE button of the color scale can be pressed by operating the input circuit 20, at the timing when a focused position of the moving PI has become a desired color. Then, the initial scale setting part 39 alters a color scale, at the timing when the INITIALIZE button has been pressed, to the initial color scale. Therefore, when the RWD button of the moving PI is pressed by operating the input circuit 20, playing the moving PI can be restarted constantly in a state where the focused position is indicated with a desired color, by display processing in the scale initialization instruction part 40.

In the case where PIs in the F side and the L side have been generated using the biplane type of X-ray diagnostic apparatus 6 or PIs corresponding to different times, such as before and after a procedure, have been generated, positions which are anatomically the same can also be displayed in a same color by synchronous processing in the color synchronization part 42, besides the display processing as described above.

That is, the medical image processing apparatus 1 as described above is configured to generate a moving PI, on which blood vessels are depicted in colors according to inflow times or arrival times of a contrast agent or the like, and display the generated moving PI under appropriate display conditions.

(Effects)

Therefore, the medical image processing apparatus 1 allows perceiving a blood flow dynamic state very easily. Specifically, a moving PI on which blood vessels are depicted in colors according to inflow times or arrival times of a contrast agent or the like can be displayed in addition to the conventional subtraction moving image on which a temporal flow of a contrast agent is depicted. In particular, a moving PI can be played continuously until an instruction to stop the moving PI is input. Furthermore, display conditions, such as playing speeds and playing periods, of a subtraction moving image and a moving PI can be easily adjusted through a GUI. When plural moving PIs are displayed in parallel, colors can also be synchronized. As a result, a subtraction moving image and a moving PI can be displayed, for perceiving a blood flow dynamic state, under appropriate display conditions according to a diagnostic purpose.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
    processing circuitry configured to:
        obtain time changes in intensity of image signals corresponding to a contrast agent or a blood flow based on at least one of time series contrast image data of an object, time series non-contrast image data of the object, and time series subtraction image data of the object between the time series contrast image data and the time series non-contrast image data,
        generate color image data, having color pixel values based on the time changes in the image signals, according to a color scale, and
        display frames of the color image data sequentially on a display,
    wherein the processing circuitry is configured to perform a loop playing of the frames of the color image data by sequentially shifting the color scale in a direction of a color phase change, the color scale being shifted at pixels of the color image data, the loop playing being performed until an instruction for stopping the loop playing is input from an input circuit.

2. The medical image processing apparatus of claim 1, wherein the processing circuitry is configured to perform the loop playing of the frames of the color image data until the instruction for stopping the loop playing is input from the input circuit, colors changing along a color circle at the pixels of the color image data.

3. The medical image processing apparatus of claim 1, wherein the processing circuitry is configured to continuously change at least one parameter out of an R value, a G value, and a B value between the frames of the color image data.

4. The medical image processing apparatus of claim 1, wherein the processing circuitry is configured to display a first moving image and a second moving image in parallel, the first moving image being obtained as the color image data by shifting the color scale, the second moving image consisting of the time series contrast image data or the time series subtraction image data.

5. The medical image processing apparatus of claim 4, wherein the processing circuitry is configured to apply an affine transformation to one of the first moving image and the second moving image in synchronization with the affine transformation applied to another of the first moving image and the second moving image.

6. The medical image processing apparatus of claim 4, wherein the processing circuitry is configured to independently adjust a playing speed of the first moving image and a playing speed of the second moving image.

7. The medical image processing apparatus of claim 4, wherein the processing circuitry is configured to play the second moving image consisting of the time series contrast image data or the time series subtraction image data in a predetermined period.

8. The medical image processing apparatus of claim 4, wherein the processing circuitry is configured to play the second moving image consisting of the time series contrast image data or the time series subtraction image data in a period determined based on a minimum value and a maximum value of times at which concentrations of the contrast agent or intensities of the image signals inside a focused region become a specific condition.

9. The medical image processing apparatus of claim 8, wherein the processing circuitry is configured to play the second moving image consisting of the time series contrast image data or the time series subtraction image data in a period of which a start time is a time obtained by subtracting a first margin time from the minimum value and an end time is a time obtained by adding a second margin time to the maximum value.

10. The medical image processing apparatus of claim 9, wherein the processing circuitry is configured to set the first margin time longer than the second margin time.

11. The medical image processing apparatus of claim 1, wherein the processing circuitry is configured to display a shift amount of the color scale on the display or another display.

12. The medical image processing apparatus of claim 11, wherein the processing circuitry is configured to display the shift amount of the color scale with a moving point or a line segment, the moving point moving corresponding to a unicursal figure of which a starting point and an ending point are on a same position, the line segment connecting the moving point with a static point.

13. The medical image processing apparatus of claim 12, wherein the unicursal figure is a circle.

14. The medical image processing apparatus of claim 1, wherein the processing circuitry has a circuit configured to set an initial position of the color scale.

15. The medical image processing apparatus of claim 1, wherein the processing circuitry includes a circuit configured to instruct setting the color scale to an initial color scale.

16. The medical image processing apparatus of claim 1, wherein the processing circuitry is configured to display two color image data sets corresponding to different imaging directions when the two color image data sets have been generated, the two color image data sets being continuously displayed as moving images respectively on the display, the two color image data sets being displayed with synchronous processing for displaying positions on blood vessels, corresponding between the two color image data sets, in a same color.

17. The medical image processing apparatus of claim 1, wherein the processing circuitry is configured to display two color image data sets corresponding to different imaging times when the two color image data sets have been generated, the two color image data sets being continuously displayed as moving images respectively on the display, the two color image data sets being displayed with synchronous processing for displaying two points in a same color, one of the two points being designated directly or indirectly to one of the two color image data sets, another of the two points being designated directly or indirectly to another of the two color image data sets.

18. The medical image processing apparatus of claim 17, wherein the processing circuitry is configured to perform the synchronous processing for shifting and expanding or contracting the color scale relatively to times at which intensities of the image signals become a specific condition, other two points being displayed in another same color by the synchronous processing, one of the other two points being designated directly or indirectly to one of the two color image data sets, another of the other two points being designated directly or indirectly to another of the two color image data sets.

19. An X-ray diagnostic apparatus comprising:
an X-ray tube and an X-ray detector for acquiring at least time series X-ray contrast image data of an object; and
processing circuitry configured to:
obtain time changes in concentration of a contrast agent based on the time series X-ray contrast image data or subtraction image data between the time series X-ray contrast image data and time series X-ray non-contrast image data,
generate color image data, having color pixel values based on the time changes in the concentration of the contrast agent, according to a color scale, and
display frames of the color image data sequentially on a display,
wherein the processing circuitry is configured to perform a loop playing of the frames of the color image data by sequentially shifting the color scale in a direction of a color phase change, the color scale being shifted at pixels of the color image data, the loop playing being performed until an instruction for stopping the loop playing is input from an input circuit.

20. A medical image processing method comprising:
obtaining time changes in intensity of image signals corresponding to a contrast agent or a blood flow based on at least one of time series contrast image data of an object, time series non-contrast image data of the object, and time series subtraction image data of the object between the time series contrast image data and the time series non-contrast image data;

generating color image data, having color pixel values based on the time changes in the image signals, according to a color scale; and displaying frames of the color image data sequentially on a display, wherein displaying the frames of the color image data includes a loop playing of the frames of the color image data by sequentially shifting the color scale in a direction of a color phase change, the color scale being shifted at pixels of the color image data, the loop playing being performed until an instruction for stopping the loop playing is input from an input circuit.

21. An X-ray diagnostic method comprising:

acquiring at least time series X-ray contrast image data of an object;

obtaining time changes in concentration of a contrast agent based on the time series X-ray contrast image data or subtraction image data between the time series X-ray contrast image data and time series X-ray non-contrast image data;

generating color image data, having color pixel values based on the time changes in the concentration of the contrast agent, according to a color scale; and displaying frames of the color image data sequentially on a display, wherein displaying the frames of the color image data includes a loop playing of the frames of the color image data by sequentially shifting the color scale in a direction of a color phase change, the color scale being shifted at pixels of the color image data, the loop playing being performed until an instruction for stopping the loop playing is input from an input circuit.

* * * * *